US012171820B2

(12) United States Patent
Poirot et al.

(10) Patent No.: US 12,171,820 B2
(45) Date of Patent: Dec. 24, 2024

(54) METHOD FOR GENERATING IMMUNE CELLS RESISTANT TO ARGININE AND/OR TRYPTOPHAN DEPLETED MICROENVIRONMENT

(71) Applicant: CELLECTIS, Paris (FR)

(72) Inventors: Laurent Poirot, San Diego, CA (US); Mathieu Simon, Paris (FR)

(73) Assignee: CELLECTIS

( * ) Notice: Subject to any disclaimer, the term of this patent is extended or adjusted under 35 U.S.C. 154(b) by 779 days.

(21) Appl. No.: 16/993,160

(22) Filed: Aug. 13, 2020

(65) Prior Publication Data

US 2020/0384094 A1 Dec. 10, 2020

Related U.S. Application Data

(62) Division of application No. 15/302,913, filed as application No. PCT/EP2015/057865 on Apr. 10, 2015, now Pat. No. 10,765,728.

(30) Foreign Application Priority Data

Apr. 11, 2014 (DK) .............................. PA201470209

(51) Int. Cl.
| | |
|---|---|
| *A61K 35/17* | (2015.01) |
| *A61K 39/00* | (2006.01) |
| *C07K 14/47* | (2006.01) |
| *C07K 14/725* | (2006.01) |
| *C12N 9/12* | (2006.01) |

(52) U.S. Cl.
CPC ...... *A61K 39/001102* (2018.08); *A61K 35/17* (2013.01); *A61K 39/0011* (2013.01); *A61K 39/001104* (2018.08); *A61K 39/001112* (2018.08); *A61K 39/001129* (2018.08); *C07K 14/4703* (2013.01); *C07K 14/4705* (2013.01); *C07K 14/7051* (2013.01); *C12N 9/12* (2013.01); *C12Y 207/11001* (2013.01); *A61K 2039/515* (2013.01)

(58) Field of Classification Search
CPC ..................................................... A61K 35/17
See application file for complete search history.

(56) References Cited

U.S. PATENT DOCUMENTS

| | | | |
|---|---|---|---|
| 4,683,195 | A | 7/1987 | Mullis et al. |
| 5,858,358 | A | 1/1999 | June et al. |
| 5,883,223 | A | 3/1999 | Gray |
| 6,010,613 | A | 1/2000 | Walters et al. |
| 6,352,694 | B1 | 3/2002 | June et al. |
| 6,534,055 | B1 | 3/2003 | June et al. |
| 6,692,964 | B1 | 2/2004 | June et al. |
| 6,797,514 | B2 | 9/2004 | Berenson et al. |
| 6,867,041 | B2 | 3/2005 | Berenson et al. |
| 6,887,466 | B2 | 5/2005 | June et al. |
| 6,905,680 | B2 | 6/2005 | June et al. |
| 6,905,681 | B1 | 6/2005 | June et al. |
| 6,905,874 | B2 | 6/2005 | Berenson et al. |
| 7,067,318 | B2 | 6/2006 | June et al. |
| 7,144,575 | B2 | 12/2006 | June et al. |
| 7,172,869 | B2 | 2/2007 | June et al. |
| 7,175,843 | B2 | 2/2007 | June et al. |
| 7,232,566 | B2 | 6/2007 | June et al. |
| 2006/0121005 | A1 | 6/2006 | Berenson et al. |
| 2011/0058957 | A1 | 3/2011 | Von Arx et al. |

FOREIGN PATENT DOCUMENTS

| | | | |
|---|---|---|---|
| WO | WO 2004/083379 | 9/2004 | |
| WO | WO 2006/097854 | 9/2006 | |
| WO | WO-2008067195 A2 * | 6/2008 | ........... C12Q 1/6883 |
| WO | WO 2011/159369 | 12/2011 | |
| WO | WO 2012/012667 | 1/2012 | |
| WO | WO 2012/138927 | 10/2012 | |
| WO | WO-2013070563 A1 * | 5/2013 | ......... C07K 14/4703 |
| WO | WO 2013/126712 | 8/2013 | |
| WO | WO 2013/176915 | 11/2013 | |
| WO | WO 2013/176916 | 11/2013 | |
| WO | WO-2013176916 A1 * | 11/2013 | ............. A61K 35/17 |
| WO | WO 2014/018601 | 1/2014 | |
| WO | WO 2014/039523 | 3/2014 | |
| WO | WO 2014/184744 | 11/2014 | |
| WO | WO 2014/189628 | 11/2014 | |
| WO | WO 2014/191128 | 12/2014 | |

OTHER PUBLICATIONS

Tam et al. (2006, Blood, vol. 107(10), pp. 4090-4100 (Year: 2006).*
Munn et al. (2005, Immunity, vol. 22, pp. 633-642 (Year: 2005).*
Ashwell and Klusner, "Genetic and mutational analysis of the T-cell antigen receptor," Annu. Rev. Immunol., 8:139-67, Apr. 1990.
Betts et al., "Sensitive and viable identification of antigen-specific CD8+ T cells by a flow cytometric assay for degranulation," J. Immunol. Methods, 281(1-2):65-78, Oct. 2003.
Bierer et al., "Cyclosporin A and FK506: molecular mechanisms of immunosuppression and probes for transplantation biology," Curr. Opin. Immunol., 5(5):763-73, Oct. 1993.
Boch et al., "Breaking the code of DNA binding specificity of TAL-type III effectors," Science, 326(5959):1509-12, Dec. 2009.

(Continued)

*Primary Examiner* — Anoop K Singh
*Assistant Examiner* — David A Montanari
(74) *Attorney, Agent, or Firm* — Fish & Richardson P.C.

(57) ABSTRACT

The present invention pertains to engineered immune cells, method for their preparation and their use as medicament, particularly for immunotherapy. The engineered immune cells of the present invention are characterized in that at least one gene selected from a gene encoding GCN2 and a gene encoding PRDM1 is inactivated or repressed. Such modified Immune cells are resistant to an arginine and/or tryptophan depleted microenvironment caused by, e.g., tumor cells, which makes the immune cells of the invention particularly suitable for immunotherapy. The invention opens the way to standard and affordable adoptive immunotherapy strategies using immune cells for treating different types of malignancies.

19 Claims, 3 Drawing Sheets

Specification includes a Sequence Listing.

(56) References Cited

OTHER PUBLICATIONS

Cambier, "Antigen and Fc receptor signaling. The awesome power of the immunoreceptor tyrosine-based activation motif (ITAM)," J. Immunol., 155(7):3281-5, Oct. 1995.
Cong et al., "Multiplex genome engineering using CRISPR/Cas systems," Science, 339(6121): 819-23, Feb. 2013.
Critchlow and Jackson, "DNA end-joining: from yeast to man," Trends Biochem Sci., 23(10):394-8, Oct. 1998.
Deltcheva et al., "CRISPR RNA maturation by trans-encoded small RNA and host factor RNase III," Nature, 471(7340):602-7, Mar. 2011.
Doyle et al., "TAL Effector-Nucleotide Targeter (TALE-NT) 2.0: tools for TAL effector design and target prediction," Nucleic. Acids Res., 40(W1):W117-22, Jul. 2012.
Gasiunas et al., "Cas9-crRNA ribonucleoprotein complex mediates specific DNA cleavage for adaptive immunity in bacteria," Proc. Natl. Acad. Sci. USA., 109(39):E2579-86, Sep. 2012.
GenBank Association No. NG_029115.1, "Homo sapiens PR/SET domain 1 (PRDM1), RefSeqGene on chromosome 6," Jul. 21, 2016, 9 pages.
GenBank Association No. NG_034053.1, "*Homo sapiens* eukaryotic translation initiation factor 2 alpha kinase 4 (EIF2AK4), RefSeqGene on chromosome 15," Jun. 5, 2015, 28 pages.
GenBank Association No. NP_001013725.2, "eIF-2-alpha kinase GCN2 [*Homo sapiens*]," Sep. 10, 2016, 5 pages.
GenBank Association No. NP001189.2, "PR domain zinc finger protein 1 isoform 1 [*Homo sapiens*], " Jul. 20, 2016, 4 pages.
Grandea et al., "Impaired assembly yet normal trafficking of MHC class I molecules in Tapasin mutant mice," Immunity, 13(2):213-222, Aug. 2000.
Henderson et al., "Comparison of the effects of FK-506, cyclosporin A and rapamycin on IL-2 production," Immunology, 73(3):316-21, Jul. 1991.
Jena et al., "Redirecting T-cell specificity by introducing a tumor-specific chimeric antigen receptor," Blood, 116(7):1035-44, Aug. 2010.
Jinek et al., "A programmable dual-RNA-guided DNA endonuclease in adaptive bacterial immunity," Science, 337(6096):816-21, Jun. 2012.
Lindstrom et al., "Indoleamine 2,3-dioxygenase activity and expression in patients with chronic lymphocytic leukemia," Clin. Lymphoma Myeloma Leuk., 12(5):363-5, Oct. 2012.
Liu et al., "Calcineurin is a common target of cyclophilin-cyclosporin A and FKBP-FK506 complexes," Cell., 66(4):807-15, Aug. 1991.
Ma et al., "Yeast Mre11 and Rad1 proteins define a Ku-independent mechanism to repair double-strand breaks lacking overlapping end sequences, " Mol. Cell Biol., 23(23):8820-8, Dec. 2003.
Mali et al., "RNA-guided human genome engineering via Cas9," Science, 339(6121):823-6, Feb. 2013.
Metzger et al., The receptor with high affinity for immunoglobulin E, Annu. Rev. Immunol., 4:419-70, 1986.
Moscou and Bogdanove, "A simple cipher governs DNA recognition by TAL effectors," Science, 326(5959):1501, Dec. 2009.
Munn et al., "Expression of indoleamine 2,3-dioxygenase by plasmacytoid dendritic cells in tumor-draining lymph nodes," J.Clin. Invest., 114(2):280-209, Jul. 2004.
Park et al., "Treating cancer with genetically engineered T cells," Trends Biotechnol., 29(11):550-7, Nov. 2011.
Rodriguez et al., "L-arginine availability regulates T-lymphocyte cell-cycle progression," Blood, 109(4):1568-73, Feb. 2007.
Rutella et al., "Indoleamine 2,3-dioxygenase-1 (IDO1) expression by childhood acute myeloid leukemia restrains IFNgamma production by T cells and may portend an unfavourable prognosis (P2157)," J. Immunol. Therapy Cancer, 1(Suppl 1)P172, Nov. 2013.
Stoddard, "Homing endonuclease structure and function," Q. Rev. Biophys., 38(1):49-95, Feb. 2005.
Suer et al., "Arginase and ornithine, as markers in human non-small cell lung carcinoma," Cancer Biochem. Biophys., 17(1-2):125-31, Jul. 1999.
Swarts et al., "DNA-guided DNA interference by a prokaryotic Argonaute," Nature, 507(7491):258-261, Mar. 2014.
Swarts et al., "The evolutionary journey of Argonaute proteins," Nat. Struct. Mol. Biol., 21(9):743-753, Sep. 2014.
Urnov et al., "Genome editing with engineered zinc finger nucleases," Nat. Rev. Gen., 11(9):636-646, Sep. 2010.
Fallarino et al., "The combined effects of tryptophan starvation and tryptophan catabolites down-regulate T cell receptor zeta-chain and induce a regulatory phenotype in naive T cells," J. Immunol., Jun. 2006, 176(11):6752-6761.
International Search Report in International Appln. No. PCT/EP2015/057865, mailed on Jun. 11, 2015, 6 pages.
Morrow et al., "Anti-leukemic mechanisms of pegylated arginase I in acute lymphoblastic T-cell leukemia," Leukemia, Aug. 2012, 27(3):569-577.
Salehi et al., "B Lymphocyte-Induced Maturation Protein-1 Contributes to Intestinal Mucosa Homeostasis by Limiting the No. of IL-17-Producing CD4(+) T Cells," J. Immunol., Dec. 2012, 189(12):5682-5693.
Seddiki et al., "The microRNA-9/B-lymphocyte-induced maturation protein-1/IL-2 axis is differentially regulated in progressive HIV infection," J. Immunol., Feb. 2013, 43(2):510-520.
Cooper et al., "Immunobiological barriers to xenotransplantation," Int. J. Surg., Nov. 2015, 23(Pt B):211-216.
Dean, "Blood Groups and Red Cell Antigens," NCBI, 2005, Chapter 2, pp. i-86.
Ekser et al., "Clinical xenotransplantation: the next medical revolution? ," Lancet, Feb. 2012, 379(9816):672-683.
Engelhardt, "Molecular mechanisms involved in T cell migration across the blood-brain barrier," J. Neural Transm., Apr. 2006, 113(4):477-485.
Fehling et al., "MHC Class I Expression in Mice Lacking the Proteasome Subunit LMP-7," Science, Aug. 1994, 265(5176):1234-1237.
Fesnak et al., "Engineered T cells: the promise and challenges of cancer immunotherapy," Nat. Rev. Cancer, Aug. 2016, 16(9):566-581.
Garbi et al., "Impaired immune responses and altered peptide repertoire in tapasin-deficient mice," Nat. Immunol., Sep. 2000, 1(3):234-238.
International Type Search Report issued in DK 201470209, dated Sep. 1, 2014.
Klingemann, "Challenges of cancer therapy with natural killer cells," Cytotherapy, Mar. 2015, 17(3):245-249.
Lin et al., "Coagulation dysregulation as a barrier to xenotransplantation in the primate," Transplant Immunol., Jun. 2009, 21(2):75-80.
Mussai et al., "Acute myeloid leukemia creates an arginase-dependent immunosuppressive microenvironment," Blood, 2013, 122(5):749-758.
Pasqualucci et al., "Inactivation of the PRDM1/BLIMP1 gene in diffuse large B cell lymphoma," J. Exp. Med., Feb. 2006, 203(2):311-317.
Rodriguez et al., "Arginase I production in the tumor microenvironment by mature myeloid cells inhibits T-cell receptor expression and antigen-specific T-cell responses," Cancer Res., Aug. 2004, 64(16):5839-5849.
Rotondo et al., "Arginase 2 is expressed by human lung cancer, but it neither induces immune suppression, nor affects disease progression," Int. J. Cancer, Sep. 2008, 123(5):1108-1116.
Santangelo et al., "Immunosuppression and Multiple Primary Malignancies in Kidney-Transplanted Patients: A Single-Institute Study," Biomed. Res. Int., Jun. 2015, 2015:183523, 8 pages.
Sharpe et al., "Genetically modified T cells in cancer therapy: opportunities and challenges," Dis. Model. Mech., Apr. 2015, 8(4):337-350.

\* cited by examiner

SEQUENCE LISTING

```
<160> NUMBER OF SEQ ID NOS: 53

<210> SEQ ID NO 1
<211> LENGTH: 1649
<212> TYPE: PRT
<213> ORGANISM: Homo sapiens

<400> SEQUENCE: 1

Met Ala Gly Gly Arg Gly Ala Pro Gly Arg Gly Arg Asp Glu Pro Pro
1               5                   10                  15

Glu Ser Tyr Pro Gln Arg Gln Asp His Glu Leu Gln Ala Leu Glu Ala
            20                  25                  30

Ile Tyr Gly Ala Asp Phe Gln Asp Leu Arg Pro Asp Ala Cys Gly Pro
        35                  40                  45

Val Lys Glu Pro Pro Glu Ile Asn Leu Val Leu Tyr Pro Gln Gly Leu
    50                  55                  60

Thr Gly Glu Glu Val Tyr Val Lys Val Asp Leu Arg Val Lys Cys Pro
65                  70                  75                  80

Pro Thr Tyr Pro Asp Val Val Pro Glu Ile Glu Leu Lys Asn Ala Lys
                85                  90                  95

Gly Leu Ser Asn Glu Ser Val Asn Leu Leu Lys Ser Arg Leu Glu Glu
            100                 105                 110

Leu Ala Lys Lys His Cys Gly Glu Val Met Ile Phe Glu Leu Ala Tyr
        115                 120                 125

His Val Gln Ser Phe Leu Ser Glu His Asn Lys Pro Pro Pro Lys Ser
    130                 135                 140

Phe His Glu Glu Met Leu Glu Arg Arg Ala Gln Glu Glu Gln Gln Arg
145                 150                 155                 160

Leu Leu Glu Ala Lys Arg Lys Glu Glu Glu Gln Arg Glu Ile Leu
                165                 170                 175

His Glu Ile Gln Arg Arg Lys Glu Glu Ile Lys Glu Glu Lys Lys Arg
            180                 185                 190

Lys Glu Met Ala Lys Gln Glu Arg Leu Glu Ile Ala Ser Leu Ser Asn
        195                 200                 205

Gln Asp His Thr Ser Lys Lys Asp Pro Gly Gly His Arg Thr Ala Ala
    210                 215                 220

Ile Leu His Gly Gly Ser Pro Asp Phe Val Gly Asn Gly Lys His Arg
```

-continued

```
            225                 230                 235                 240
Ala Asn Ser Ser Gly Arg Ser Arg Arg Glu Arg Gln Tyr Ser Val Cys
                    245                 250                 255
Asn Ser Glu Asp Ser Pro Gly Ser Cys Glu Ile Leu Tyr Phe Asn Met
                    260                 265                 270
Gly Ser Pro Asp Gln Leu Met Val His Lys Gly Lys Cys Ile Gly Ser
                    275                 280                 285
Asp Glu Gln Leu Gly Lys Leu Val Tyr Asn Ala Leu Glu Thr Ala Thr
                    290                 295                 300
Gly Gly Phe Val Leu Leu Tyr Glu Trp Val Leu Gln Trp Gln Lys Lys
305                 310                 315                 320
Met Gly Pro Phe Leu Thr Ser Gln Glu Lys Glu Lys Ile Asp Lys Cys
                    325                 330                 335
Lys Lys Gln Ile Gln Gly Thr Glu Thr Glu Phe Asn Ser Leu Val Lys
                    340                 345                 350
Leu Ser His Pro Asn Val Val Arg Tyr Leu Ala Met Asn Leu Lys Glu
                    355                 360                 365
Gln Asp Asp Ser Ile Val Val Asp Ile Leu Val Glu His Ile Ser Gly
                    370                 375                 380
Val Ser Leu Ala Ala His Leu Ser His Ser Gly Pro Ile Pro Val His
385                 390                 395                 400
Gln Leu Arg Arg Tyr Thr Ala Gln Leu Leu Ser Gly Leu Asp Tyr Leu
                    405                 410                 415
His Ser Asn Ser Val Val His Lys Val Leu Ser Ala Ser Asn Val Leu
                    420                 425                 430
Val Asp Ala Glu Gly Thr Val Lys Ile Thr Asp Tyr Ser Ile Ser Lys
                    435                 440                 445
Arg Leu Ala Asp Ile Cys Lys Glu Asp Val Phe Glu Gln Thr Arg Val
                    450                 455                 460
Arg Phe Ser Asp Asn Ala Leu Pro Tyr Lys Thr Gly Lys Lys Gly Asp
465                 470                 475                 480
Val Trp Arg Leu Gly Leu Leu Leu Ser Leu Ser Gln Gly Gln Glu
                    485                 490                 495
Cys Gly Glu Tyr Pro Val Thr Ile Pro Ser Asp Leu Pro Ala Asp Phe
                    500                 505                 510
Gln Asp Phe Leu Lys Lys Cys Val Cys Leu Asp Asp Lys Glu Arg Trp
                    515                 520                 525
Ser Pro Gln Gln Leu Leu Lys His Ser Phe Ile Asn Pro Gln Pro Lys
                    530                 535                 540
Met Pro Leu Val Glu Gln Ser Pro Glu Asp Ser Gly Gln Asp Tyr
545                 550                 555                 560
Val Glu Thr Val Ile Pro Ser Asn Arg Leu Pro Ser Ala Ala Phe Phe
                    565                 570                 575
Ser Glu Thr Gln Arg Gln Phe Ser Arg Tyr Phe Ile Glu Phe Glu Glu
                    580                 585                 590
Leu Gln Leu Leu Gly Lys Gly Ala Phe Gly Ala Val Ile Lys Val Gln
                    595                 600                 605
Asn Lys Leu Asp Gly Cys Cys Tyr Ala Val Lys Arg Ile Pro Ile Asn
                    610                 615                 620
Pro Ala Ser Arg Gln Phe Arg Arg Ile Lys Gly Glu Val Thr Leu Leu
625                 630                 635                 640
Ser Arg Leu His His Glu Asn Ile Val Arg Tyr Tyr Asn Ala Trp Ile
                    645                 650                 655
```

```
Glu Arg His Glu Arg Pro Ala Gly Pro Gly Thr Pro Pro Asp Ser
            660             665             670

Gly Pro Leu Ala Lys Asp Asp Arg Ala Ala Arg Gly Gln Pro Ala Ser
        675             680             685

Asp Thr Asp Gly Leu Asp Ser Val Glu Ala Ala Pro Pro Ile
690             695             700

Leu Ser Ser Ser Val Glu Trp Ser Thr Ser Gly Glu Arg Ser Ala Ser
705             710             715             720

Ala Arg Phe Pro Ala Thr Gly Pro Gly Ser Ser Asp Asp Glu Asp Asp
                725             730             735

Asp Glu Asp Glu His Gly Gly Val Phe Ser Gln Ser Phe Leu Pro Ala
        740             745             750

Ser Asp Ser Glu Ser Asp Ile Ile Phe Asp Asn Glu Asp Glu Asn Ser
        755             760             765

Lys Ser Gln Asn Gln Asp Glu Asp Cys Asn Glu Lys Asn Gly Cys His
        770             775             780

Glu Ser Glu Pro Ser Val Thr Thr Glu Ala Val His Tyr Leu Tyr Ile
785             790             795             800

Gln Met Glu Tyr Cys Glu Lys Ser Thr Leu Arg Asp Thr Ile Asp Gln
                805             810             815

Gly Leu Tyr Arg Asp Thr Val Arg Leu Trp Arg Leu Phe Arg Glu Ile
                820             825             830

Leu Asp Gly Leu Ala Tyr Ile His Glu Lys Gly Met Ile His Arg Asp
                835             840             845

Leu Lys Pro Val Asn Ile Phe Leu Asp Ser Asp His Val Lys Ile
        850             855             860

Gly Asp Phe Gly Leu Ala Thr Asp His Leu Ala Phe Ser Ala Asp Ser
865             870             875             880

Lys Gln Asp Asp Gln Thr Gly Asp Leu Ile Lys Ser Asp Pro Ser Gly
                885             890             895

His Leu Thr Gly Met Val Gly Thr Ala Leu Tyr Val Ser Pro Glu Val
            900             905             910

Gln Gly Ser Thr Lys Ser Ala Tyr Asn Gln Lys Val Asp Leu Phe Ser
        915             920             925

Leu Gly Ile Ile Phe Phe Glu Met Ser Tyr His Pro Met Val Thr Ala
        930             935             940

Ser Glu Arg Ile Phe Val Leu Asn Gln Leu Arg Asp Pro Thr Ser Pro
945             950             955             960

Lys Phe Pro Glu Asp Phe Asp Asp Gly Glu His Ala Lys Gln Lys Ser
                965             970             975

Val Ile Ser Trp Leu Leu Asn His Asp Pro Ala Lys Arg Pro Thr Ala
        980             985             990

Thr Glu Leu Leu Lys Ser Glu Leu Leu Pro Pro Pro Gln Met Glu Glu
            995             1000            1005

Ser Glu Leu His Glu Val Leu His His Thr Leu Thr Asn Val Asp
    1010            1015            1020

Gly Lys Ala Tyr Arg Thr Met Met Ala Gln Ile Phe Ser Gln Arg
    1025            1030            1035

Ile Ser Pro Ala Ile Asp Tyr Thr Tyr Asp Ser Asp Ile Leu Lys
    1040            1045            1050

Gly Asn Phe Ser Ile Arg Thr Ala Lys Met Gln Gln His Val Cys
    1055            1060            1065
```

-continued

Glu Thr Ile Ile Arg Ile Phe Lys Arg His Gly Ala Val Gln Leu
1070              1075                  1080

Cys Thr Pro Leu Leu Leu Pro Arg Asn Arg Gln Ile Tyr Glu His
1085              1090                  1095

Asn Glu Ala Ala Leu Phe Met Asp His Ser Gly Met Leu Val Met
1100              1105                  1110

Leu Pro Phe Asp Leu Arg Ile Pro Phe Ala Arg Tyr Val Ala Arg
1115              1120                  1125

Asn Asn Ile Leu Asn Leu Lys Arg Tyr Cys Ile Glu Arg Val Phe
1130              1135                  1140

Arg Pro Arg Lys Leu Asp Arg Phe His Pro Lys Glu Leu Leu Glu
1145              1150                  1155

Cys Ala Phe Asp Ile Val Thr Ser Thr Thr Asn Ser Phe Leu Pro
1160              1165                  1170

Thr Ala Glu Ile Ile Tyr Thr Ile Tyr Glu Ile Ile Gln Glu Phe
1175              1180                  1185

Pro Ala Leu Gln Glu Arg Asn Tyr Ser Ile Tyr Leu Asn His Thr
1190              1195                  1200

Met Leu Leu Lys Ala Ile Leu Leu His Cys Gly Ile Pro Glu Asp
1205              1210                  1215

Lys Leu Ser Gln Val Tyr Ile Ile Leu Tyr Asp Ala Val Thr Glu
1220              1225                  1230

Lys Leu Thr Arg Arg Glu Val Glu Ala Lys Phe Cys Asn Leu Ser
1235              1240                  1245

Leu Ser Ser Asn Ser Leu Cys Arg Leu Tyr Lys Phe Ile Glu Gln
1250              1255                  1260

Lys Gly Asp Leu Gln Asp Leu Met Pro Thr Ile Asn Ser Leu Ile
1265              1270                  1275

Lys Gln Lys Thr Gly Ile Ala Gln Leu Val Lys Tyr Gly Leu Lys
1280              1285                  1290

Asp Leu Glu Glu Val Val Gly Leu Leu Lys Lys Leu Gly Ile Lys
1295              1300                  1305

Leu Gln Val Leu Ile Asn Leu Gly Leu Val Tyr Lys Val Gln Gln
1310              1315                  1320

His Asn Gly Ile Ile Phe Gln Phe Val Ala Phe Ile Lys Arg Arg
1325              1330                  1335

Gln Arg Ala Val Pro Glu Ile Leu Ala Ala Gly Gly Arg Tyr Asp
1340              1345                  1350

Leu Leu Ile Pro Gln Phe Arg Gly Pro Gln Ala Leu Gly Pro Val
1355              1360                  1365

Pro Thr Ala Ile Gly Val Ser Ile Ala Ile Asp Lys Ile Ser Ala
1370              1375                  1380

Ala Val Leu Asn Met Glu Glu Ser Val Thr Ile Ser Ser Cys Asp
1385              1390                  1395

Leu Leu Val Val Ser Val Gly Gln Met Ser Met Ser Arg Ala Ile
1400              1405                  1410

Asn Leu Thr Gln Lys Leu Trp Thr Ala Gly Ile Thr Ala Glu Ile
1415              1420                  1425

Met Tyr Asp Trp Ser Gln Ser Gln Glu Glu Leu Gln Glu Tyr Cys
1430              1435                  1440

Arg His His Glu Ile Thr Tyr Val Ala Leu Val Ser Asp Lys Glu
1445              1450                  1455

Gly Ser His Val Lys Val Lys Ser Phe Glu Lys Glu Arg Gln Thr

```
              1460                1465                1470

Glu  Lys  Arg  Val  Leu  Glu  Thr  Glu  Leu  Val  Asp  His  Val  Leu  Gln
          1475                1480                1485

Lys  Leu  Arg  Thr  Lys  Val  Thr  Asp  Glu  Arg  Asn  Gly  Arg  Glu  Ala
          1490                1495                1500

Ser  Asp  Asn  Leu  Ala  Val  Gln  Asn  Leu  Lys  Gly  Ser  Phe  Ser  Asn
          1505                1510                1515

Ala  Ser  Gly  Leu  Phe  Glu  Ile  His  Gly  Ala  Thr  Val  Val  Pro  Ile
          1520                1525                1530

Val  Ser  Val  Leu  Ala  Pro  Glu  Lys  Leu  Ser  Ala  Ser  Thr  Arg  Arg
          1535                1540                1545

Arg  Tyr  Glu  Thr  Gln  Val  Gln  Thr  Arg  Leu  Gln  Thr  Ser  Leu  Ala
          1550                1555                1560

Asn  Leu  His  Gln  Lys  Ser  Ser  Glu  Ile  Glu  Ile  Leu  Ala  Val  Asp
          1565                1570                1575

Leu  Pro  Lys  Glu  Thr  Ile  Leu  Gln  Phe  Leu  Ser  Leu  Glu  Trp  Asp
          1580                1585                1590

Ala  Asp  Glu  Gln  Ala  Phe  Asn  Thr  Thr  Val  Lys  Gln  Leu  Leu  Ser
          1595                1600                1605

Arg  Leu  Pro  Lys  Gln  Arg  Tyr  Leu  Lys  Leu  Val  Cys  Asp  Glu  Ile
          1610                1615                1620

Tyr  Asn  Ile  Lys  Val  Glu  Lys  Lys  Val  Ser  Val  Leu  Phe  Leu  Tyr
          1625                1630                1635

Ser  Tyr  Arg  Asp  Asp  Tyr  Tyr  Arg  Ile  Leu  Phe
          1640                1645

<210> SEQ ID NO 2
<211> LENGTH: 825
<212> TYPE: PRT
<213> ORGANISM: Homo sapiens

<400> SEQUENCE: 2

Met  Leu  Asp  Ile  Cys  Leu  Glu  Lys  Arg  Val  Gly  Thr  Thr  Leu  Ala  Ala
1                   5                   10                  15

Pro  Lys  Cys  Asn  Ser  Ser  Thr  Val  Arg  Phe  Gln  Gly  Leu  Ala  Glu  Gly
                    20                  25                  30

Thr  Lys  Gly  Thr  Met  Lys  Met  Asp  Met  Glu  Asp  Ala  Asp  Met  Thr  Leu
                35                  40                  45

Trp  Thr  Glu  Ala  Glu  Phe  Glu  Glu  Lys  Cys  Thr  Tyr  Ile  Val  Asn  Asp
        50                  55                  60

His  Pro  Trp  Asp  Ser  Gly  Ala  Asp  Gly  Gly  Thr  Ser  Val  Gln  Ala  Glu
65                  70                  75                  80

Ala  Ser  Leu  Pro  Arg  Asn  Leu  Leu  Phe  Lys  Tyr  Ala  Thr  Asn  Ser  Glu
                85                  90                  95

Glu  Val  Ile  Gly  Val  Met  Ser  Lys  Glu  Tyr  Ile  Pro  Lys  Gly  Thr  Arg
                100                 105                 110

Phe  Gly  Pro  Leu  Ile  Gly  Glu  Ile  Tyr  Thr  Asn  Asp  Thr  Val  Pro  Lys
            115                 120                 125

Asn  Ala  Asn  Arg  Lys  Tyr  Phe  Trp  Arg  Ile  Tyr  Ser  Arg  Gly  Glu  Leu
        130                 135                 140

His  His  Phe  Ile  Asp  Gly  Phe  Asn  Glu  Glu  Lys  Ser  Asn  Trp  Met  Arg
145                 150                 155                 160

Tyr  Val  Asn  Pro  Ala  His  Ser  Pro  Arg  Glu  Gln  Asn  Leu  Ala  Ala  Cys
                165                 170                 175
```

```
Gln Asn Gly Met Asn Ile Tyr Phe Tyr Thr Ile Lys Pro Ile Pro Ala
                180                 185                 190

Asn Gln Glu Leu Leu Val Trp Tyr Cys Arg Asp Phe Ala Glu Arg Leu
            195                 200                 205

His Tyr Pro Tyr Pro Gly Glu Leu Thr Met Met Asn Leu Thr Gln Thr
        210                 215                 220

Gln Ser Ser Leu Lys Gln Pro Ser Thr Glu Lys Asn Glu Leu Cys Pro
225                 230                 235                 240

Lys Asn Val Pro Lys Arg Glu Tyr Ser Val Lys Glu Ile Leu Lys Leu
                245                 250                 255

Asp Ser Asn Pro Ser Lys Gly Lys Asp Leu Tyr Arg Ser Asn Ile Ser
            260                 265                 270

Pro Leu Thr Ser Glu Lys Asp Leu Asp Asp Phe Arg Arg Arg Gly Ser
        275                 280                 285

Pro Glu Met Pro Phe Tyr Pro Arg Val Val Tyr Pro Ile Arg Ala Pro
        290                 295                 300

Leu Pro Glu Asp Phe Leu Lys Ala Ser Leu Ala Tyr Gly Ile Glu Arg
305                 310                 315                 320

Pro Thr Tyr Ile Thr Arg Ser Pro Ile Pro Ser Ser Thr Thr Pro Ser
                325                 330                 335

Pro Ser Ala Arg Ser Ser Pro Asp Gln Ser Leu Lys Ser Ser Ser Pro
            340                 345                 350

His Ser Ser Pro Gly Asn Thr Val Ser Pro Val Gly Pro Gly Ser Gln
        355                 360                 365

Glu His Arg Asp Ser Tyr Ala Tyr Leu Asn Ala Ser Tyr Gly Thr Glu
        370                 375                 380

Gly Leu Gly Ser Tyr Pro Gly Tyr Ala Pro Leu Pro His Leu Pro Pro
385                 390                 395                 400

Ala Phe Ile Pro Ser Tyr Asn Ala His Tyr Pro Lys Phe Leu Leu Pro
                405                 410                 415

Pro Tyr Gly Met Asn Cys Asn Gly Leu Ser Ala Val Ser Ser Met Asn
            420                 425                 430

Gly Ile Asn Asn Phe Gly Leu Phe Pro Arg Leu Cys Pro Val Tyr Ser
        435                 440                 445

Asn Leu Leu Gly Gly Gly Ser Leu Pro His Pro Met Leu Asn Pro Thr
450                 455                 460

Ser Leu Pro Ser Ser Leu Pro Ser Asp Gly Ala Arg Arg Leu Leu Gln
465                 470                 475                 480

Pro Glu His Pro Arg Glu Val Leu Val Pro Ala Pro His Ser Ala Phe
                485                 490                 495

Ser Phe Thr Gly Ala Ala Ala Ser Met Lys Asp Lys Ala Cys Ser Pro
            500                 505                 510

Thr Ser Gly Ser Pro Thr Ala Gly Thr Ala Thr Ala Glu His Val
        515                 520                 525

Val Gln Pro Lys Ala Thr Ser Ala Ala Met Ala Pro Ser Ser Asp
530                 535                 540

Glu Ala Met Asn Leu Ile Lys Asn Lys Arg Asn Met Thr Gly Tyr Lys
545                 550                 555                 560

Thr Leu Pro Tyr Pro Leu Lys Lys Gln Asn Gly Lys Ile Lys Tyr Glu
                565                 570                 575

Cys Asn Val Cys Ala Lys Thr Phe Gly Gln Leu Ser Asn Leu Lys Val
            580                 585                 590

His Leu Arg Val His Ser Gly Glu Arg Pro Phe Lys Cys Gln Thr Cys
```

```
                    595                 600                 605
Asn Lys Gly Phe Thr Gln Leu Ala His Leu Gln Lys His Tyr Leu Val
            610                 615                 620
His Thr Gly Glu Lys Pro His Glu Cys Gln Val Cys His Lys Arg Phe
625                 630                 635                 640
Ser Ser Thr Ser Asn Leu Lys Thr His Leu Arg Leu His Ser Gly Glu
                645                 650                 655
Lys Pro Tyr Gln Cys Lys Val Cys Pro Ala Lys Phe Thr Gln Phe Val
            660                 665                 670
His Leu Lys Leu His Lys Arg Leu His Thr Arg Glu Arg Pro His Lys
            675                 680                 685
Cys Ser Gln Cys His Lys Asn Tyr Ile His Leu Cys Ser Leu Lys Val
            690                 695                 700
His Leu Lys Gly Asn Cys Ala Ala Ala Pro Ala Pro Gly Leu Pro Leu
705                 710                 715                 720
Glu Asp Leu Thr Arg Ile Asn Glu Glu Ile Glu Lys Phe Asp Ile Ser
                725                 730                 735
Asp Asn Ala Asp Arg Leu Glu Asp Val Glu Asp Ile Ser Val Ile
            740                 745                 750
Ser Val Val Glu Lys Glu Ile Leu Ala Val Val Arg Lys Glu Lys Glu
            755                 760                 765
Glu Thr Gly Leu Lys Val Ser Leu Gln Arg Asn Met Gly Asn Gly Leu
770                 775                 780
Leu Ser Ser Gly Cys Ser Leu Tyr Glu Ser Ser Asp Leu Pro Leu Met
785                 790                 795                 800
Lys Leu Pro Pro Ser Asn Pro Leu Pro Leu Val Pro Val Lys Val Lys
                805                 810                 815
Gln Glu Thr Val Glu Pro Met Asp Pro
            820                 825

<210> SEQ ID NO 3
<211> LENGTH: 49
<212> TYPE: DNA
<213> ORGANISM: Homo sapiens

<400> SEQUENCE: 3
tggatttgag ggttaaatgc ccacctacct atccagatgt gtgagtaca          49

<210> SEQ ID NO 4
<211> LENGTH: 49
<212> TYPE: DNA
<213> ORGANISM: Homo sapiens

<400> SEQUENCE: 4
ttgtaggaaa tggtaaacat cgggcaaact cctcaggaag gtctaggta          49

<210> SEQ ID NO 5
<211> LENGTH: 495
<212> TYPE: PRT
<213> ORGANISM: Artificial Sequence
<220> FEATURE:
<223> OTHER INFORMATION: anti-CD19 Cimeric Antigen Receptor

<400> SEQUENCE: 5

Met Glu Thr Asp Thr Leu Leu Leu Trp Val Leu Leu Leu Trp Val Pro
1               5                   10                  15
Gly Ser Thr Gly Glu Val Gln Leu Gln Gln Ser Gly Pro Glu Leu Ile
            20                  25                  30
```

```
Lys Pro Gly Ala Ser Val Lys Met Ser Cys Lys Ala Ser Gly Tyr Thr
                35                  40                  45

Phe Thr Ser Tyr Val Met His Trp Val Lys Gln Lys Pro Gly Gln Gly
    50                  55                  60

Leu Glu Trp Ile Gly Tyr Ile Asn Pro Tyr Asn Asp Gly Thr Lys Tyr
65                  70                  75                  80

Asn Glu Lys Phe Lys Gly Lys Ala Thr Leu Thr Ser Asp Lys Ser Ser
                85                  90                  95

Ser Thr Ala Tyr Met Glu Leu Ser Ser Leu Thr Ser Glu Asp Ser Ala
                100                 105                 110

Val Tyr Tyr Cys Ala Arg Gly Thr Tyr Tyr Gly Ser Arg Val Phe
                115                 120                 125

Asp Tyr Trp Gly Gln Gly Thr Thr Leu Thr Val Ser Ser Gly Gly Gly
    130                 135                 140

Gly Ser Gly Gly Gly Gly Ser Gly Gly Gly Gly Ser Asp Ile Val Met
145                 150                 155                 160

Thr Gln Ala Ala Pro Ser Ile Pro Val Thr Pro Gly Glu Ser Val Ser
                165                 170                 175

Ile Ser Cys Arg Ser Ser Lys Ser Leu Leu Asn Ser Asn Gly Asn Thr
                180                 185                 190

Tyr Leu Tyr Trp Phe Leu Gln Arg Pro Gly Gln Ser Pro Gln Leu Leu
                195                 200                 205

Ile Tyr Arg Met Ser Asn Leu Ala Ser Gly Val Pro Asp Arg Phe Ser
                210                 215                 220

Gly Ser Gly Ser Gly Thr Ala Phe Thr Leu Arg Ile Ser Arg Val Glu
225                 230                 235                 240

Ala Glu Asp Val Gly Val Tyr Tyr Cys Met Gln His Leu Glu Tyr Pro
                245                 250                 255

Phe Thr Phe Gly Ala Gly Thr Lys Leu Glu Leu Lys Arg Ser Asp Pro
                260                 265                 270

Thr Thr Thr Pro Ala Pro Arg Pro Pro Thr Pro Ala Pro Thr Ile Ala
                275                 280                 285

Ser Gln Pro Leu Ser Leu Arg Pro Glu Ala Cys Arg Pro Ala Ala Gly
                290                 295                 300

Gly Ala Val His Thr Arg Gly Leu Asp Phe Ala Cys Asp Ile Tyr Ile
305                 310                 315                 320

Trp Ala Pro Leu Ala Gly Thr Cys Gly Val Leu Leu Leu Ser Leu Val
                325                 330                 335

Ile Thr Leu Tyr Cys Lys Arg Gly Arg Lys Lys Leu Leu Tyr Ile Phe
                340                 345                 350

Lys Gln Pro Phe Met Arg Pro Val Gln Thr Thr Gln Glu Glu Asp Gly
                355                 360                 365

Cys Ser Cys Arg Phe Pro Glu Glu Glu Glu Gly Gly Cys Glu Leu Arg
370                 375                 380

Val Lys Phe Ser Arg Ser Ala Asp Ala Pro Ala Tyr Gln Gln Gly Gln
385                 390                 395                 400

Asn Gln Leu Tyr Asn Glu Leu Asn Leu Gly Arg Arg Glu Glu Tyr Asp
                405                 410                 415

Val Leu Asp Lys Arg Arg Gly Arg Asp Pro Glu Met Gly Gly Lys Pro
                420                 425                 430

Arg Arg Lys Asn Pro Gln Glu Gly Leu Tyr Asn Glu Leu Gln Lys Asp
                435                 440                 445
```

Lys Met Ala Glu Ala Tyr Ser Glu Ile Gly Met Lys Gly Glu Arg Arg
                450                 455                 460

Arg Gly Lys Gly His Asp Gly Leu Tyr Gln Gly Leu Ser Thr Ala Thr
465                 470                 475                 480

Lys Asp Thr Tyr Asp Ala Leu His Met Gln Ala Leu Pro Pro Arg
                485                 490                 495

<210> SEQ ID NO 6
<211> LENGTH: 251
<212> TYPE: PRT
<213> ORGANISM: Artificial Sequence
<220> FEATURE:
<223> OTHER INFORMATION: Anti-CD19 CAR

<400> SEQUENCE: 6

Glu Val Gln Leu Gln Gln Ser Gly Pro Glu Leu Ile Lys Pro Gly Ala
1               5                   10                  15

Ser Val Lys Met Ser Cys Lys Ala Ser Gly Tyr Thr Phe Thr Ser Tyr
                20                  25                  30

Val Met His Trp Val Lys Gln Lys Pro Gly Gln Gly Leu Glu Trp Ile
            35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Gly Thr Tyr Tyr Gly Ser Arg Val Phe Asp Tyr Trp Gly
            100                 105                 110

Gln Gly Thr Thr Leu Thr Val Ser Ser Gly Gly Gly Ser Gly Gly
        115                 120                 125

Gly Gly Ser Gly Gly Gly Ser Asp Ile Val Met Thr Gln Ala Ala
    130                 135                 140

Pro Ser Ile Pro Val Thr Pro Gly Glu Ser Val Ser Ile Ser Cys Arg
145                 150                 155                 160

Ser Ser Lys Ser Leu Leu Asn Ser Asn Gly Asn Thr Tyr Leu Tyr Trp
                165                 170                 175

Phe Leu Gln Arg Pro Gly Gln Ser Pro Gln Leu Leu Ile Tyr Arg Met
            180                 185                 190

Ser Asn Leu Ala Ser Gly Val Pro Asp Arg Phe Ser Gly Ser Gly Ser
        195                 200                 205

Gly Thr Ala Phe Thr Leu Arg Ile Ser Arg Val Glu Ala Glu Asp Val
    210                 215                 220

Gly Val Tyr Tyr Cys Met Gln His Leu Glu Tyr Pro Phe Thr Phe Gly
225                 230                 235                 240

Ala Gly Thr Lys Leu Glu Leu Lys Arg Ala Asp
                245                 250

<210> SEQ ID NO 7
<211> LENGTH: 23
<212> TYPE: DNA
<213> ORGANISM: Homo sapiens

<400> SEQUENCE: 7
gagaatcaaa atcggtgaat agg                                    23

<210> SEQ ID NO 8

```
<211> LENGTH: 23
<212> TYPE: DNA
<213> ORGANISM: Homo sapiens

<400> SEQUENCE: 8
ttcaaaacct gtcagtgatt ggg                                              23

<210> SEQ ID NO 9
<211> LENGTH: 23
<212> TYPE: DNA
<213> ORGANISM: Homo sapiens

<400> SEQUENCE: 9
tgtgctagac atgaggtcta tgg                                              23

<210> SEQ ID NO 10
<211> LENGTH: 23
<212> TYPE: DNA
<213> ORGANISM: Homo sapiens

<400> SEQUENCE: 10
cgtcatgagc agattaaacc cgg                                              23

<210> SEQ ID NO 11
<211> LENGTH: 23
<212> TYPE: DNA
<213> ORGANISM: Homo sapiens

<400> SEQUENCE: 11
tcagggttct ggatatctgt ggg                                              23

<210> SEQ ID NO 12
<211> LENGTH: 23
<212> TYPE: DNA
<213> ORGANISM: Homo sapiens

<400> SEQUENCE: 12
gtcagggttc tggatatctg tgg                                              23

<210> SEQ ID NO 13
<211> LENGTH: 23
<212> TYPE: DNA
<213> ORGANISM: Homo sapiens

<400> SEQUENCE: 13
ttcggaaccc aatcactgac agg                                              23

<210> SEQ ID NO 14
<211> LENGTH: 23
<212> TYPE: DNA
<213> ORGANISM: Homo sapiens

<400> SEQUENCE: 14
taaacccggc cactttcagg agg                                              23

<210> SEQ ID NO 15
<211> LENGTH: 23
<212> TYPE: DNA
<213> ORGANISM: Homo sapiens

<400> SEQUENCE: 15
aaagtcagat ttgttgctcc agg                                              23
```

```
<210> SEQ ID NO 16
<211> LENGTH: 23
<212> TYPE: DNA
<213> ORGANISM: Homo sapiens

<400> SEQUENCE: 16
aacaaatgtg tcacaaagta agg                                              23

<210> SEQ ID NO 17
<211> LENGTH: 23
<212> TYPE: DNA
<213> ORGANISM: Homo sapiens

<400> SEQUENCE: 17
tggatttaga gtctctcagc tgg                                              23

<210> SEQ ID NO 18
<211> LENGTH: 23
<212> TYPE: DNA
<213> ORGANISM: Homo sapiens

<400> SEQUENCE: 18
taggcagaca gacttgtcac tgg                                              23

<210> SEQ ID NO 19
<211> LENGTH: 23
<212> TYPE: DNA
<213> ORGANISM: Homo sapiens

<400> SEQUENCE: 19
agctggtaca cggcagggtc agg                                              23

<210> SEQ ID NO 20
<211> LENGTH: 23
<212> TYPE: DNA
<213> ORGANISM: Homo sapiens

<400> SEQUENCE: 20
gctggtacac ggcagggtca ggg                                              23

<210> SEQ ID NO 21
<211> LENGTH: 23
<212> TYPE: DNA
<213> ORGANISM: Homo sapiens

<400> SEQUENCE: 21
tctctcagct ggtacacggc agg                                              23

<210> SEQ ID NO 22
<211> LENGTH: 23
<212> TYPE: DNA
<213> ORGANISM: Homo sapiens

<400> SEQUENCE: 22
tttcaaaacc tgtcagtgat tgg                                              23

<210> SEQ ID NO 23
<211> LENGTH: 23
<212> TYPE: DNA
<213> ORGANISM: Homo sapiens

<400> SEQUENCE: 23
gattaaaccc ggccactttc agg                                              23
```

```
<210> SEQ ID NO 24
<211> LENGTH: 23
<212> TYPE: DNA
<213> ORGANISM: Homo sapiens

<400> SEQUENCE: 24
ctcgaccagc ttgacatcac agg                                          23

<210> SEQ ID NO 25
<211> LENGTH: 23
<212> TYPE: DNA
<213> ORGANISM: Homo sapiens

<400> SEQUENCE: 25
agagtctctc agctggtaca cgg                                          23

<210> SEQ ID NO 26
<211> LENGTH: 23
<212> TYPE: DNA
<213> ORGANISM: Homo sapiens

<400> SEQUENCE: 26
ctctcagctg gtacacggca ggg                                          23

<210> SEQ ID NO 27
<211> LENGTH: 23
<212> TYPE: DNA
<213> ORGANISM: Homo sapiens

<400> SEQUENCE: 27
aagttcctgt gatgtcaagc tgg                                          23

<210> SEQ ID NO 28
<211> LENGTH: 23
<212> TYPE: DNA
<213> ORGANISM: Homo sapiens

<400> SEQUENCE: 28
atcctcctcc tgaaagtggc cgg                                          23

<210> SEQ ID NO 29
<211> LENGTH: 23
<212> TYPE: DNA
<213> ORGANISM: Homo sapiens

<400> SEQUENCE: 29
tgctcatgac gctgcggctg tgg                                          23

<210> SEQ ID NO 30
<211> LENGTH: 23
<212> TYPE: DNA
<213> ORGANISM: Homo sapiens

<400> SEQUENCE: 30
acaaaactgt gctagacatg agg                                          23

<210> SEQ ID NO 31
<211> LENGTH: 23
<212> TYPE: DNA
<213> ORGANISM: Homo sapiens

<400> SEQUENCE: 31
atttgtttga gaatcaaaat cgg                                          23
```

<210> SEQ ID NO 32
<211> LENGTH: 23
<212> TYPE: DNA
<213> ORGANISM: Homo sapiens

<400> SEQUENCE: 32
catcacagga actttctaaa agg                                                 23

<210> SEQ ID NO 33
<211> LENGTH: 23
<212> TYPE: DNA
<213> ORGANISM: Homo sapiens

<400> SEQUENCE: 33
gtcgagaaaa gctttgaaac agg                                                 23

<210> SEQ ID NO 34
<211> LENGTH: 23
<212> TYPE: DNA
<213> ORGANISM: Homo sapiens

<400> SEQUENCE: 34
ccactttcag gaggaggatt cgg                                                 23

<210> SEQ ID NO 35
<211> LENGTH: 23
<212> TYPE: DNA
<213> ORGANISM: Homo sapiens

<400> SEQUENCE: 35
ctgacaggtt ttgaaagttt agg                                                 23

<210> SEQ ID NO 36
<211> LENGTH: 23
<212> TYPE: DNA
<213> ORGANISM: Homo sapiens

<400> SEQUENCE: 36
agctttgaaa caggtaagac agg                                                 23

<210> SEQ ID NO 37
<211> LENGTH: 23
<212> TYPE: DNA
<213> ORGANISM: Homo sapiens

<400> SEQUENCE: 37
tggaataatg ctgttgttga agg                                                 23

<210> SEQ ID NO 38
<211> LENGTH: 23
<212> TYPE: DNA
<213> ORGANISM: Homo sapiens

<400> SEQUENCE: 38
agagcaacag tgctgtggcc tgg                                                 23

<210> SEQ ID NO 39
<211> LENGTH: 23
<212> TYPE: DNA
<213> ORGANISM: Homo sapiens

<400> SEQUENCE: 39
ctgtggtcca gctgaggtga ggg                                               23

<210> SEQ ID NO 40
<211> LENGTH: 23
<212> TYPE: DNA
<213> ORGANISM: Homo sapiens

<400> SEQUENCE: 40
ctgcggctgt ggtccagctg agg                                               23

<210> SEQ ID NO 41
<211> LENGTH: 23
<212> TYPE: DNA
<213> ORGANISM: Homo sapiens

<400> SEQUENCE: 41
tgtggtccag ctgaggtgag ggg                                               23

<210> SEQ ID NO 42
<211> LENGTH: 23
<212> TYPE: DNA
<213> ORGANISM: Homo sapiens

<400> SEQUENCE: 42
cttcttcccc agcccaggta agg                                               23

<210> SEQ ID NO 43
<211> LENGTH: 23
<212> TYPE: DNA
<213> ORGANISM: Homo sapiens

<400> SEQUENCE: 43
acacggcagg gtcagggttc tgg                                               23

<210> SEQ ID NO 44
<211> LENGTH: 23
<212> TYPE: DNA
<213> ORGANISM: Homo sapiens

<400> SEQUENCE: 44
cttcaagagc aacagtgctg tgg                                               23

<210> SEQ ID NO 45
<211> LENGTH: 23
<212> TYPE: DNA
<213> ORGANISM: Homo sapiens

<400> SEQUENCE: 45
ctggggaaga aggtgtcttc tgg                                               23

<210> SEQ ID NO 46
<211> LENGTH: 23
<212> TYPE: DNA
<213> ORGANISM: Homo sapiens

<400> SEQUENCE: 46
tcctcctcct gaaagtggcc ggg                                               23

<210> SEQ ID NO 47
<211> LENGTH: 23
<212> TYPE: DNA
<213> ORGANISM: Homo sapiens

<400> SEQUENCE: 47

```
ttaatctgct catgacgctg cgg                                               23

<210> SEQ ID NO 48
<211> LENGTH: 23
<212> TYPE: DNA
<213> ORGANISM: Homo sapiens

<400> SEQUENCE: 48
acccggccac tttcaggagg agg                                               23

<210> SEQ ID NO 49
<211> LENGTH: 23
<212> TYPE: DNA
<213> ORGANISM: Homo sapiens

<400> SEQUENCE: 49
ttcttcccca gcccaggtaa ggg                                               23

<210> SEQ ID NO 50
<211> LENGTH: 23
<212> TYPE: DNA
<213> ORGANISM: Homo sapiens

<400> SEQUENCE: 50
cttacctggg ctggggaaga agg                                               23

<210> SEQ ID NO 51
<211> LENGTH: 23
<212> TYPE: DNA
<213> ORGANISM: Homo sapiens

<400> SEQUENCE: 51
gacaccttct tccccagccc agg                                               23

<210> SEQ ID NO 52
<211> LENGTH: 23
<212> TYPE: DNA
<213> ORGANISM: Homo sapiens

<400> SEQUENCE: 52
gctgtggtcc agctgaggtg agg                                               23

<210> SEQ ID NO 53
<211> LENGTH: 23
<212> TYPE: DNA
<213> ORGANISM: Homo sapiens

<400> SEQUENCE: 53
ccgaatcctc ctcctgaaag tgg                                               23
```

METHOD FOR GENERATING IMMUNE CELLS RESISTANT TO ARGININE AND/OR TRYPTOPHAN DEPLETED MICROENVIRONMENT

CROSS-REFERENCE TO RELATED APPLICATIONS

This application is a divisional of U.S. application Ser. No. 15/302,913, filed Oct. 7, 2016, which is a National Stage entry under 35 U.S.C. § 371 of International Application No. PCT/EP2015/057865, filed Apr. 10, 2015, which claims priority to Danish Patent Application No. PA201470209, filed Apr. 11, 2014. The disclosure of the prior applications are hereby incorporated in their entirety by reference.

FIELD OF THE INVENTION

The present invention pertains to engineered immune cells, such as T-cells, method for their preparation and their use as medicament, particularly for immunotherapy. The engineered immune cells of the present invention are characterized in that at least one gene selected from a gene encoding GCN2 (general control nonderepressible 2; also known as eukaryotic translation initiation factor 2 alpha kinase 4, EIFF2AK4) and a gene encoding PRDM1 (PR domain containing 1, with ZNF domain; also known as B lymphocyte-induced maturation protein 1, BLIMP-1) is inactivated or repressed. Such modified immune cells are resistant to an arginine and/or tryptophan depleted microenvironment caused by, e.g., tumor cells, which makes the immune cells of the invention particularly suitable for immunotherapy. The invention opens the way to standard and affordable adoptive immunotherapy strategies using immune cells for treating different types of malignancies.

BACKGROUND OF THE INVENTION

Cellular adaptive immunity is mediated by T-lymphocytes, also known as T-cells, which upon recognition of a non-self or tumoral antigen can either destroy the target cell or orchestrate an immune response with other cells of the immune system.

Adoptive immunotherapy, which involves the transfer of autologous antigen-specific T cells generated ex vivo, is a promising strategy to treat viral infections and cancer. The T-cells used for adoptive immunotherapy can be generated either by expansion of antigen-specific T cells or redirection of T-cells through genetic engineering (Park, Rosenberg et al. 2011). Transfer of viral antigen specific T-cells is a well-established procedure used for the treatment of transplant associated viral infections and rare viral-related malignancies. Similarly, isolation and transfer of tumor specific T-cells have been shown to be successful in treating melanoma.

Novel specificities in T-cells have been successfully generated through the genetic transfer of transgenic T cell receptors or chimeric antigen receptors (CARs) (Jena, Dotti et al. 2010). CARs are synthetic receptors consisting of a targeting moiety that is associated with one or more signaling domains in a single fusion molecule. In general, the binding moiety of a CAR consists of an antigen-binding domain of a single-chain antibody (scFv), comprising the light and variable fragments of a monoclonal antibody joined by a flexible linker. Binding moieties based on receptor or ligand domains have also been used successfully. The signaling domains for first generation CARs are derived from the cytoplasmic region of the CD3zeta or the Fc receptor gamma chains. First generation CARs have been shown to successfully redirect T cell cytotoxicity, however, they failed to provide prolonged expansion and anti-tumor activity in vivo. Signaling domains from co-stimulatory molecules including CD28, OX-40 (CD134), and 4-1BB (CD137) have been added alone (second generation) or in combination (third generation) to enhance survival and increase proliferation of CAR modified T-cells. CARs have successfully allowed T-cells to be redirected against antigens expressed at the surface of tumor cells from various malignancies including lymphomas and solid tumors (Jena, Dotti et al. 2010).

While it is thus possible to redirect T-cell cytotoxicity towards tumor cells, these later cells may still dampen the immune response by escape mechanisms. One such escape mechanism is the elimination of certain amino acids such as arginine and tryptophan from their local microenvironment by production of arginase and Indoleamine 2,3-dioxygenase (IDO1).

Most reports have associated arginase activity with the need for malignant cells to produce polyamines to sustain their rapid proliferation. However, arginase tends to inhibit T-cell proliferation and activation.

Rodriguez et al. (2004) found that L-arginine (L-Arg) plays a central role in several biologic systems including the regulation of T-cell function. L-Arg depletion by myeloid-derived suppressor cells producing arginase I is seen in patients with cancer inducing T-cell anergy. They showed that L-Arg starvation could regulate T-cell-cycle progression insofar as T cells cultured in the absence of L-Arg are arrested in the G0-G1phase of the cell cycle. This was associated with an inability of T cells to up-regulate cyclin D3 and cyclin-dependent kinase 4 (cdk4). Silencing of cyclin D3 reproduced the cell cycle arrest caused by L-Arg starvation. They also found that Signaling through GCN2 kinase was triggered during amino acid starvation.

A recent study demonstrated that arginase is expressed and released from Leukemia blasts and is present at high concentrations in the plasma of patients with acute myeloid leukemia (AML), resulting in suppression of T-cell proliferation (Mussai, F. et al. 2013). The study showed that the immunosuppressive activity of AML blasts can be modulated through small molecule inhibitors of arginase and inducible nitric oxide synthase, strongly supporting the hypothesis that AML creates an immunosuppressive microenvironment that contributes to the pancytopenia observed at diagnosis. High arginase activity has been also described in patients with solid tumors, in particular in gastric, colon, breast, and lung cancers, and more particularly in small cell lung carcinoma (Suer et al., 1999). It is also considered that the following reaction catalyzed by arginase+H2O→urea+ornithine increases urea and ornithine concentration is the environment of tumors, which may have a negative impact on lymphocytes. On another hand, the inhibition of arginase in vivo was found to decrease tumor growth in mice as per the study by Rodriguez et al. (2004).

The metabolic enzyme IDO1 contributes to the balance between tolerance versus inflammation in a number of experimental models. Expression of IDO1 in APCs, such as macrophages and dendritic cells, can suppress T cell responses as observed during mammalian pregnancy, inflammatory conditions, autoimmunity and tumor resistance. IDO1 was found to be over-expressed by plasmacytoid dendritic cells in tumor draining lymph nodes (Munn, D. H. et al., 2004) as well as in child acute myeloid leukemia (AML) (Rutella, S. et al., 2013) and patients with chronic lymphocytic leukemia (Lindstrom V., et al. 2013). IDO1 catabolizes the essential amino acid tryptophan, thus decreasing concentrations in the local microenvironment as well as generating biologically active downstream metabolites. Studies in both yeast and mice revealed that GCN2 also plays a role in the response to tryptophan deprivation. PRDM1 (also referred to as BLIMP-1) is a protein, which expression level parallels that of IDO1, and that is up-regulated in situation of tryptophan deprivation.

It thus appears that production of arginase and/or IDO1, through amino acid deprivation, represents a significant component of tumor escape, which needs to be addressed by innovative immunotherapy strategies, especially those involving T-cells.

SUMMARY OF THE INVENTION

The above need is addressed, according to the present invention, by repressing or disrupting GCN2 and/or PRDM1 protein formation in immune cells, such as T-cells, to make them resistant to arginine and/or tryptophan depletion. Through the experiments shown in the present specification, GCN2 and PRDM1 proteins are found to act as sensors of arginine and/or tryptophan starvation, which can be switched off to avoid anergy of immune cells, particularly T-cells, without significantly dampening their activity. The resulting immune cells remain in condition to proliferate in the local microenvironment of arginase producing cells, and thus are prompt to confer an improved immune response against tumors.

According to one aspect, the present invention provides a method for preparing an engineered immune cell, in particular an engineered T cell, comprising:

modifying an immune cell, such as a T-cell, by inactivating or repressing a gene encoding GCN2 (such as human GCN2 or a functional variant thereof) and/or a gene encoding PRDM1 (such as human PRDM1 or a functional variant thereof).

According to certain embodiments, the immune cell is modified by inactivating a gene encoding GCN2 (e.g., the human GCN2 gene; NCBI Reference Sequence: NG_034053.1). The inactivation of the GCN2 gene may, for instance, be achieved by genome modification, more particularly through the expression in the immune cell of a rare-cutting endonuclease able to selectively inactivate said gene by DNA cleavage, preferably double-strand break. Such rare-cutting endonuclease may be a TALE-nuclease, meganuclease, zinc-finger nuclease (ZFN), or RNA guided endonuclease.

According to particular embodiments, the immune cell is a human immune cell which is modified by inactivating a gene encoding human GCN2 as set forth in SEQ ID NO: 1 (NCBI Reference Sequence: NP_001013725.2) or a functional variant thereof which has at least about 80%, such as at least about 85%, at least about 90%, at least about 95%, at least about 96%, at least about 97%, at least about 98% or at least about 99%, sequence identity with the human GCN2 set forth in SEQ ID NO: 1 over the entire length of SEQ ID NO: 1.

According to certain embodiments, the immune cell is modified by repressing a gene encoding GCN2 (e.g., the human GCN2 gene; NCBI Reference Sequence: NG_034053.1).

According to certain other embodiments, the immune cell is modified by inactivating a gene encoding PRDM1 (e.g., the human PRDM1 gene; NCBI Reference Sequence: NG_029115.1). The inactivation of the PRDM1 gene may, for instance, be achieved by genome modification, more particularly through the expression in the immune cell of a rare-cutting endonuclease able to selectively inactivate said gene by DNA cleavage, preferably double-strand break. Such rare-cutting endonuclease may be a TALE-nuclease, meganuclease, zinc-finger nuclease (ZFN), or RNA guided endonuclease.

According to another embodiment, said rare-cutting endonuclease is a DNA guided endonuclease. As an example, such endonuclease may be the Argonaute proteins (Ago). Ago proteins from bacteria such as *Thermus thermophilus* (strain HB27) have been recently described in bacteria to act as a barrier for the uptake and propogation of foreign DNA (Swarts D. C, et al. *Nature* 507: 258-261) In vivo, Tt Ago is loaded with 5' phosphorylated DNA guides, from 13 to 25 base pairs that are mostly plasmid derived and have a strong bias for a 5'-end deoxycytidine. These small interfering DNAs guide TtAgo cleave complementary DNA strands at high temperature (75° C.). WO2014189628A (Caribou biosciences) discloses such complex comprising an Argonaute and a designed nucleic acid-targeting nucleic acid.

According to particular embodiments, the immune cell is a human immune cell which is modified by inactivating a gene encoding human PRDM1 as set forth in SEQ ID NO: 2 (NCBI Reference Sequence: NP_001189.2) or a functional variant thereof which has at least about 80%, such as at least about 85%, at least about 90%, at least about 95%, at least about 96%, at least about 97%, at least about 98% or at least about 99%, sequence identity with human PRDM1 as set forth in SEQ ID NO: 2 over the entire length of SEQ ID NO: 2.

According to certain other embodiments, the immune cell is modified by repressing a gene encoding PRDM1 (e.g., the human PRDM1 gene; NCBI Reference Sequence: NG_029115.1).

According to certain other embodiments, the immune cell is modified by inactivating both the gene encoding GCN2 (e.g., the human GCN2 gene) and the gene encoding PRDM1 (e.g., the human PRDM1 gene). The inactivation of the GCN2 gene and PRDM1 gene may, for instance, be achieved by genome modification, more particularly through the expression in the immune cell of rare-cutting endonucleases able to selectively inactivate said genes by DNA cleavage, preferably double-strand break. Such rare-cutting endonucleases may independently be a TALE-nuclease, meganuclease, zinc-finger nuclease (ZFN), or RNA guided endonuclease.

According to particular embodiments, the immune cell may be further engineered to make it non-alloreactive, especially by inactivating one or more genes involved in self-recognition, such as those, for instance, encoding components of T-cell receptors (TCR). This can be achieved by a genome modification, more particularly through the expression in the immune cell, particular T-cell, of a rare-cutting endonuclease able to selectively inactivate by DNA cleavage, preferably double-strand break, at least one gene encoding a component of the T-Cell receptor (TCR), such as the gene encoding TCR alpha or TCR beta. Such rare-cutting endonuclease may be a TALE-nuclease, meganuclease, zing-finger nuclease (ZFN), or RNA guided endonuclease. Preferably, the rare-cutting endonuclease is able to selectively inactivate by DNA cleavage the gene coding for TCR alpha.

According to optional embodiments, the immune cell may be further engineered to express a Chimeric Antigen Receptor (CAR) directed against at least one antigen expressed at the surface of a malignant cell. Particularly, said CAR is directed against an antigen commonly expressed at the surface of solid tumor cells, such as 5T4, ROR1 and EGFRvIII. Said CAR may also be directed against an antigen commonly expressed at the surface of liquid tumors, such as CD123, or CD19.

The present invention thus provides in a further aspect engineered immune cells, in particular isolated engineered immune cells, characterized in that a gene encoding GCN2 and/or a gene encoding PRDM1 is inactivated or repressed.

According to certain embodiments, an engineered immune cell, in particular isolated engineered immune cell, is provided wherein a gene encoding GCN2 (e.g., the human GCN2 gene) is inactivated.

According to certain other embodiments, an engineered immune cell, in particular isolated engineered immune cell, is provided wherein a gene encoding GCN2 (e.g., the human GCN2 gene) is repressed.

According to certain other embodiments, an engineered immune cell, in particular isolated engineered immune cell, is provided wherein a gene encoding PRDM1 (e.g., the human PRDM1 gene) is inactivated.

According to certain other embodiments, an engineered immune cell, in particular isolated engineered immune cell, is provided wherein a gene encoding PRDM1 (e.g., the human PRDM1 gene) is repressed.

According to certain other embodiments, an engineered immune cell, in particular isolated engineered immune cell, is provided wherein both a gene encoding GCN2 (e.g., the human GCN2 gene) and a gene encoding PRDM1 (e.g., the human PRDM1 gene) are inactivated.

According to certain other embodiments, an engineered immune cell, in particular isolated engineered immune cell, is provided wherein both a gene encoding GCN2 (e.g., the human GCN2 gene) and a gene encoding PRDM1 (e.g., the human PRDM1 gene) are repressed.

According to certain other embodiments, an engineered immune cell, in particular isolated engineered immune cell, is provided wherein a gene encoding GCN2 (e.g., the human GCN2 gene) is inactivated and a gene encoding PRDM1 (e.g., the human PRDM1 gene) is repressed.

According to certain other embodiments, an engineered immune cell, in particular isolated engineered immune cell, is provided wherein a gene encoding GCN2 (e.g., the human GCN2 gene) is repressed and a gene encoding PRDM1 (e.g., the human PRDM1 gene) is inactivated.

According to certain embodiments, an immune cell is provided which expresses a rare-cutting endonuclease able to selectively inactivate by DNA cleavage in said cell a gene encoding GCN2. More particularly, such immune cell comprises an exogenous nucleic acid molecule comprising a nucleotide sequence encoding said rare-cutting endonuclease, which may be a TALE-nuclease, meganuclease, zing-finger nuclease (ZFN), or RNA guided endonuclease.

According to particular embodiments, said rare-cutting endonuclease binds to a sequence set forth in SEQ ID NO: 3. According to other particular embodiments, said rare-cutting endonuclease binds to a sequence set forth in SEQ ID NO: 4.

According to certain other embodiments, an immune cell is provided which expresses a rare-cutting endonuclease able to selectively inactivate by DNA cleavage in said cell a gene encoding PRDM1. More particularly, such immune cell comprises an exogenous nucleic acid molecule comprising a nucleotide sequence encoding said rare-cutting endonuclease, which may be a TALE-nuclease, meganuclease, zing-finger nuclease (ZFN), or RNA guided endonuclease.

According to certain other embodiments, an immune cell is provided which expresses a rare-cutting endonuclease able to selectively inactivate by DNA cleavage in said cell a gene encoding GCN2 and a rare-cutting endonuclease able to selectively inactivate by DNA cleavage in said cell a gene encoding PRDM1. More particularly, such immune cell comprises one or more exogenous nucleic acid molecules comprising one or nucleotide sequences encoding said rare-cutting endonucleases, which independently may be a TALE-nuclease, meganuclease, zing-finger nuclease (ZFN), or RNA guided endonuclease.

According to particular embodiments, the immune cell may further have at least one inactivated gene encoding a component of the TCR receptor. More particularly, such immune cell may express a rare-cutting endonuclease able to selectively inactivate by DNA cleavage, preferably double-strand break, said at least one gene encoding a component of the T-Cell receptor (TCR). Accordingly, said immune cell may comprise an exogenous nucleic acid molecule comprising a nucleotide sequence coding for a rare-cutting endonuclease able to selectively inactivate by DNA cleavage at least one gene coding for one component of the T-Cell receptor (TCR). The disruption of TCR provides a non-alloreactive immune cell that can be used in allogeneic treatment strategies.

According to optional embodiments, the immune cell may be engineered to express a Chimeric Antigen Receptor (CAR) directed against at least one antigen expressed at the surface of a malignant cell. Particularly, the immune cell comprises an exogenous nucleic acid molecule comprising a nucleotide sequence encoding said CAR. According to particular embodiments, said CAR is directed against an antigen selected from CD19, CD33, CD123, CS1, BCMA, CD38, 5T4, ROR1 and EGFRvIII. The binding of the target antigen by the CAR has the effect of triggering an immune response by the immune cell directed against the malignant cell, which results in degranulation of various cytokine and degradation enzymes in the interspace between the cells.

As a result of the present invention, engineered immune cells can be used as therapeutic products, ideally as an "off the shelf" product, for use in the treatment or prevention of medical conditions such as cancer.

Thus, the present invention further provides an engineered immune cell of the present invention or a composition, such as a pharmaceutical composition, comprising same for use as a medicament. According to certain embodiments, the engineered immune cell or composition is for use in the treatment of a cancer, and more particularly for use in the treatment of a solid or liquid tumor. According to particular embodiments, the engineered immune cell or composition is for use in the treatment of a cancer selected from the group consisting of lung cancer, small lung cancer, breast cancer, uterine cancer, prostate cancer, kidney cancer, colon cancer, liver cancer, pancreatic cancer, and skin cancer. According to other particular embodiments, the engineered immune cell or composition is for use in the treatment of a sarcoma. According to other particular embodiments, the engineered immune cell or composition is for use in the treatment of a carcinoma. According to more particular embodiments, the engineered immune cell or composition is for use in the treatment of renal, lung or colon carcinoma. According to other particular embodiments, the engineered immune cell or composition is for use in the treatment of leukemia, such as acute lymphoblastic leukemia (ALL), acute myeloid leukemia (AML), chronic lymphocytic leukemia (CLL), chronic myelogenous leukemia (CML), and chronic myelomonocystic leukemia (CMML).

According to other particular embodiments, the engineered immune cell or composition is for use in the treatment of lymphoma, such as Hodgkin's or Non-Hodgkin's lymphoma. According to certain embodiment, the engineered immune cell originates from a patient, e.g. a human patient, to be treated. According to certain other embodiment, the engineered immune cell originates from at least one donor.

It is understood that the details given herein with respect to one aspect of the invention also apply to any of the other aspects of the invention.

DETAILED DESCRIPTION OF THE INVENTION

Figure 1:
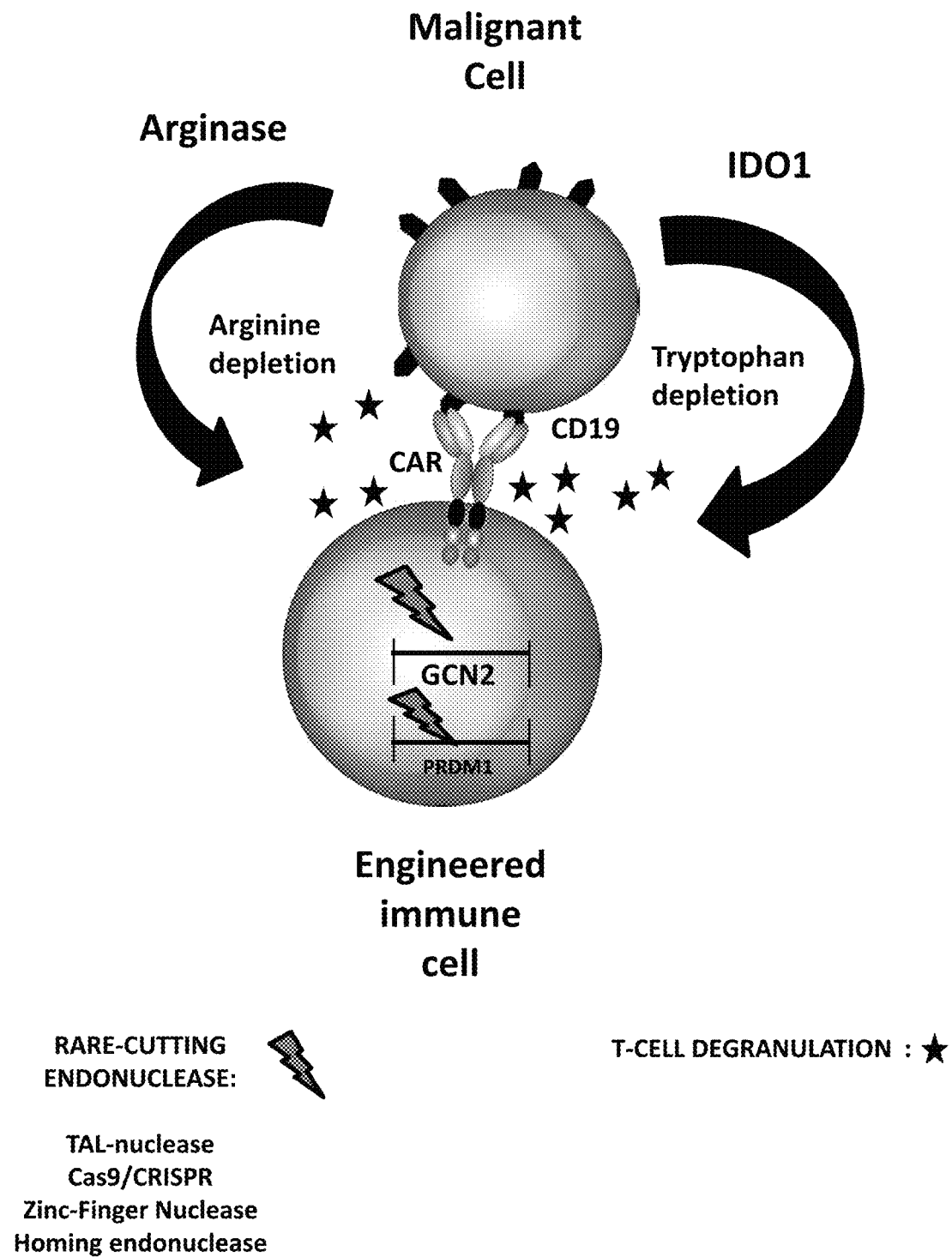
FIG. 1: Schematic representation of an engineered immune cell according to the invention expressing a rare-cutting endonuclease able to selectively inactivate by DNA cleavage a GCN2 encoding gene and/or a rare-cutting endonuclease able to selectively inactivate by DNA cleavage a PRDM1 encoding gene.

Unless specifically defined herein, all technical and scientific terms used have the same meaning as commonly understood by a skilled artisan in the fields of gene therapy, biochemistry, genetics, and molecular biology.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will prevail. Further, the materials, methods, and examples are illustrative only and are not intended to be limiting, unless otherwise specified.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Current Protocols in Molecular Biology (Frederick M. AUSUBEL, 2000, Wiley and son Inc, Library of Congress, USA); Molecular Cloning: A Laboratory Manual, Third Edition, (Sambrook et al, 2001, Cold Spring Harbor, New York: Cold Spring Harbor Laboratory Press); Oligonucleotide Synthesis (M. J. Gait ed., 1984); Mullis et al. U.S. Pat. No. 4,683,195; Nucleic Acid Hybridization (B. D. Harries & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the series, Methods In ENZYMOLOGY (J. Abelson and M. Simon, eds.-in-chief, Academic Press, Inc., New York), specifically, Vols. 154 and 155 (Wu et al. eds.) and Vol. 185, "Gene Expression Technology" (D. Goeddel, ed.); Gene Transfer Vectors For Mammalian Cells (J. H. Miller and M. P. Calos eds., 1987, Cold Spring Harbor Laboratory); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); and Manipulating the Mouse Embryo, (Cold Spring Harbor Laboratory Press, Cold Spring Harbor, N.Y., 1986).

Methods for Preparing Engineered T-Cells

In a general aspect, the present invention pertains to methods for preparing engineered immune cells, such as T-cells or natural killer (NK) cells.

Accordingly, the present invention provides a method for preparing an engineered immune cell comprising:

modifying an immune cell, such as a T-cell, by inactivating or repressing a gene encoding GCN2 (such as human GCN2 or a functional variant thereof) and/or a gene encoding PRDM1 (such as human PRDM1 or a functional variant thereof).

According to certain embodiments, the immune cell is modified by inactivating a gene encoding GCN2 (e.g., the human GCN2 gene; NCBI Reference Sequence: NG_034053.1). The inactivation of the GCN2 gene may, for instance, be achieved by genome modification, more particularly through the expression in the immune cell of a rare-cutting endonuclease able to selectively inactivate said gene by DNA cleavage.

According to particular embodiments, the immune cell is a human immune cell which is modified by inactivating a gene encoding human GCN2 as set forth in SEQ ID NO: 1 (NCBI Reference Sequence: NP_001013725.2) or a functional variant thereof which has at least about 80%, such as at least about 85%, at least about 90%, at least about 95%, at least about 96%, at least about 97%, at least about 98% or at least about 99%, sequence identity with the human GCN2 set forth in SEQ ID NO: 1 over the entire length of SEQ ID NO: 1.

According to certain other embodiments, the immune cell is modified by inactivating a gene encoding PRDM1 (e.g., the human PRDM1 gene; NCBI Reference Sequence: NG_029115.1). The inactivation of the PRDM1 gene may, for instance, be achieved by genome modification, more particularly through the expression in the immune cell of a rare-cutting endonuclease able to selectively inactivate said gene by DNA cleavage.

According to particular embodiments, the immune cell is a human immune cell which is modified by inactivating a gene encoding human PRDM1 as set forth in SEQ ID NO: 2 (NCBI Reference Sequence: NP_001189.2) or a functional variant thereof which has at least about 80%, such as at least about 85%, at least about 90%, at least about 95%, at least about 96%, at least about 97%, at least about 98% or at least about 99%, sequence identity with human PRDM1 as set forth in SEQ ID NO: 2 over the entire length of SEQ ID NO: 2.

According to certain other embodiments, the immune cell is modified by inactivating both a gene encoding GCN2 (e.g., the human GCN2 gene) and a gene encoding PRDM1 (e.g., the human PRDM1 gene). The inactivation of these genes may, for instance, be achieved by genome modification, more particularly through the expression in the immune cell of a rare-cutting endonuclease able to selectively inactivate by DNA cleavage the gene encoding GCN2 and a rare-cutting endonuclease able to selectively inactivate by DNA cleavage the gene encoding PRDM1.

By "inactivating" or "inactivation of" a gene it is intended that the gene of interest (e.g. a gene encoding GCN2 or PRDM1) is not expressed in a functional protein form. In particular embodiments, the genetic modification of the method relies on the expression, in provided cells to engineer, of a rare-cutting endonuclease such that same catalyzes cleavage in one targeted gene thereby inactivating said targeted gene. The nucleic acid strand breaks caused by the endonuclease are commonly repaired through the distinct mechanisms of homologous recombination or non-homologous end joining (NHEJ). However, NHEJ is an imperfect repair process that often results in changes to the DNA sequence at the site of the cleavage. Mechanisms involve rejoining of what remains of the two DNA ends through direct re-ligation (Critchlow and Jackson 1998) or via the so-called microhomology-mediated end joining (Betts, Brenchley et al. 2003; Ma, Kim et al. 2003). Repair via non-homologous end joining (NHEJ) often results in small insertions or deletions and can be used for the creation of specific gene knockouts. Said modification may be a substitution, deletion, or addition of at least one nucleotide. Cells in which a cleavage-induced mutagenesis event, i.e. a mutagenesis event consecutive to an NHEJ event, has occurred can be identified and/or selected by well-known method in the art.

A rare-cutting endonuclease to be used in accordance with the present invention to inactivate the gene encoding GCN2 may, for instance, be a TALE-nuclease, meganuclease, zinc-finger nuclease (ZFN), or RNA guided endonuclease (such as Cas9).

According to a particular embodiment, the rare-cutting endonuclease is a TALE-nuclease.

According to another particular embodiment, the rate-cutting endonuclease is a homing endonuclease, also known under the name of meganuclease.

According to another particular embodiment, the rare-cutting endonuclease is a zinc-finger nuclease (ZNF).

According to another particular embodiment, the rare-cutting endonuclease is a RNA guided endonuclease. According to a preferred embodiment, the RNA guided endonuclease is the Cas9/CRISPR complex.

In order to be expressed in the immune cell, a rare-cutting endonuclease used in accordance with the present invention to inactivate a gene encoding GCN2 may be introduced into the cell by way of an exogenous nucleic acid molecule comprising a nucleotide sequence encoding said rare-cutting endonuclease. Accordingly, the method of the present invention may comprise introducing into the immune cell an exogenous nucleic acid molecule comprising a nucleotide sequence encoding a rare-cutting endonuclease able to selectively inactivate by DNA cleavage a gene encoding GCN2 (e.g., the human GCN2 gene). As a result, an engineered T-cell is obtained which expresses a rare-cutting endonuclease able to selectively inactivate in said cell by DNA cleavage a gene encoding GCN2.

According to particular embodiments, the rare-cutting endonuclease targets (e.g., binds to) a sequence set forth in SEQ ID NO: 3. According to other particular embodiments, the rare-cutting endonuclease targets (e.g., binds to) a sequence set forth in SEQ ID NO: 4.

A rare-cutting endonuclease to be used in accordance with the present invention to inactivate the PRDM1 gene may, for instance, be a TALE-nuclease, meganuclease, zinc-finger nuclease (ZFN), or RNA guided endonuclease (such as Cas9).

According to a particular embodiment, the rare-cutting endonuclease is a TALE-nuclease.

According to another particular embodiment, the rate-cutting endonuclease is a homing endonuclease, also known under the name of meganuclease.

According to another particular embodiment, the rare-cutting endonuclease is a zinc-finger nuclease (ZNF).

According to another particular embodiment, the rare-cutting endonuclease is a RNA guided endonuclease. According to a preferred embodiment, the RNA guided endonuclease is the Cas9/CRISPR complex.

In order to be expressed in the T-cell, a rare-cutting endonuclease used in accordance with the present invention to inactive the gene encoding PRDM1 may be introduced into the cell by way of an exogenous nucleic acid molecule comprising a nucleotide sequence encoding said rare-cutting endonuclease. Accordingly, the method of the present invention may comprise introducing into the T-cell an exogenous nucleic acid molecule comprising a nucleotide sequence encoding a rare-cutting endonuclease able to selectively inactivate by DNA cleavage the gene encoding PRDM1 (e.g., the human PRDM1 gene). As a result, an engineered T-cell is obtained which expresses a rare-cutting endonuclease able to selectively inactivate by DNA cleavage the gene encoding PRDM1.

According to certain embodiments, the immune cell is modified by repressing a gene encoding GCN2 (e.g., the human GCN2 gene; NCBI Reference Sequence: NG_034053.1).

According to certain other embodiments, the immune cell is modified by repressing a gene encoding PRDM1 (e.g., the human PRDM1 gene; NCBI Reference Sequence: NG_029115.1).

By "repressing" or "repression of" a gene it is intended that the expression of a gene of interest (e.g. a gene encoding GCN2 or PRDM1) in a modified cell is reduced compared to the expression of said gene in an unmodified cell of the same type. In particular, "repressing" or "repression of" a gene is meant that the expression of a gene of interest (e.g. a gene encoding GCN2 or PRDM1) in a modified cell is reduced by at least about 30%, at least about 40%, at least about 50%, at least about 60%, at least about 65%, at least about 70%, at least about 75%, at least about 80%, at least about 85%, at least about 90%, at least 95%, at least about 96%, at least about 97%, at least about 98%, or at least about 99% or about 100% compared to the expression of said gene in an unmodified cell of the same type.

Repression of a gene of interested can be achieved by any suitable means known in the art. For example, the expression of a gene of interest may be reduced by gene silencing techniques such as the use of antisense oligonucleotides, ribozymes or interfering RNA (RNAi) molecules, such as microRNA (miRNA), small interfering RNA (siRNA) or short hairpin RNA (shRNA).

It is also contemplated by the present invention that the engineered immune cell, in particular in case of an engineered T-cell, of the present invention does not express a functional T-cell receptor (TCR) on its cell surface. T-cell receptors are cell surface receptors that participate in the activation of T-cells in response to the presentation of antigen. The TCR is generally made from two chains, alpha and beta, which assemble to form a heterodimer and associates with the CD3-transducing subunits to form the T-cell receptor complex present on the cell surface. Each alpha and beta chain of the TCR consists of an immunoglobulin-like N-terminal variable (V) and constant (C) region, a hydrophobic transmembrane domain, and a short cytoplasmic region. As for immunoglobulin molecules, the variable region of the alpha and beta chains are generated by V(D)J recombination, creating a large diversity of antigen specificities within the population of T cells. However, in contrast to immunoglobulins that recognize intact antigen, T-cells are activated by processed peptide fragments in association with an MHC molecule, introducing an extra dimension to antigen recognition by T cells, known as MHC restriction. Recognition of MHC disparities between the donor and recipient through the T-cell receptor leads to T-cell proliferation and the potential development of graft versus host disease (GVHD). It has been shown that normal surface expression of the TCR depends on the coordinated synthesis and assembly of all seven components of the complex (Ashwell and Klusner 1990). The inactivation of TCR alpha or TCR beta can result in the elimination of the TCR from the surface of T-cells preventing recognition of alloantigen and thus GVHD. The inactivation of at least one gene coding for a TCR component thus renders the engineered immune cell less alloreactive. By "inactivating" or "inactivation of" a gene it is meant that the gene of interest (e.g., at least one gene coding for a TCR component) is not expressed in a functional protein form.

Therefore, the method of the present invention in accordance with particular embodiments further comprises inactivating at least one gene encoding a component of the T-cell receptor. More particularly, the inactivation is achieved by using (e.g., introducing into the immune cell, such as T-cell) a rare-cutting endonuclease able to selectively inactivate by DNA cleavage, preferably double-strand break, at least one gene encoding a component of the T-cell receptor. According to particular embodiments, the rare-cutting endonuclease is able to selectively inactivate by DNA cleavage the gene coding for TCR alpha or TCR beta. According to a preferred embodiment, the rare-cutting endonuclease is able to selectively inactivate by DNA cleavage the gene coding for TCR alpha. Especially in case of an allogeneic immune cell obtained from a donor, inactivating of at least one gene encoding a component of TCR, notably TCR alpha, leads to engineered immune cells, when infused into an allogeneic host, which are non-alloreactive. This makes the engineered immune cell particular suitable for allogeneic transplantations, especially because it reduces the risk of graft versus host disease.

A rare-cutting endonuclease to be used in accordance with the present invention to inactivate at least one gene encoding a component of the T-cell receptor may, for instance, be a TALE-nuclease, meganuclease, zinc-finger nuclease (ZFN), or RNA guided endonuclease (such as Cas9).

According to a particular embodiment, the rare-cutting endonuclease is a TALE-nuclease.

According to another particular embodiment, the rare-cutting endonuclease is a homing endonuclease, also known under the name of meganuclease.

According to another particular embodiment, the rare-cutting endonuclease is a zinc-finger nuclease (ZNF).

According to another particular embodiment, the rare-cutting endonuclease is a RNA guided endonuclease. According to a preferred embodiment, the RNA guided endonuclease is the Cas9/CRISPR complex.

In order to be expressed in the immune cell, such as a T-cell, a rare-cutting endonuclease used in accordance with the present invention to inactive at least one gene encoding a component of the T-cell receptor may be introduced into the cell by way of an exogenous nucleic acid molecule comprising a nucleotide sequence encoding said rare-cutting endonuclease. Accordingly, the method of the invention may comprise introducing into said immune cell an exogenous nucleic acid molecule comprising a nucleotide sequence encoding a rare-cutting endonuclease able to selectively inactivate by DNA cleavage, preferably double-strand break, at least one gene encoding a component of the T-cell receptor.

As a result, an engineered immune cell, such as a T-cell, is obtained which further expresses a rare-cutting endonuclease able to selectively inactivate by DNA cleavage at least one gene encoding a component of the T-cell receptor. In consequence, an engineered immune cell, such as a T-cell, is obtained which is characterized in that at least one gene encoding a component of the T-cell receptor, such as TCR alpha, is inactivated.

It is also contemplated by the present invention that the engineered immune cell, such as a T-cell, further expresses a Chimeric Antigen Receptor (CAR) directed against at least one antigen expressed at the surface of a malignant cell. Hence, in accordance with certain embodiments, the method of the present invention further comprises introducing into said immune cell an exogenous nucleic acid molecule comprising a nucleotide sequence encoding a Chimeric Antigen Receptor directed against at least one antigen expressed at the surface of a malignant cell. According to particular embodiments, said CAR is directed against an antigen selected from CD19, CD33, CD123, CS1, BCMA, CD38, 5T4, ROR1 and EGFRvIII.

The immune cell to be modified according to the present invention may be any suitable immune cell. For example, the immune cell may be a T-cell or a natural killer (NK) cell. According to certain embodiments, the immune cell is a T-cell, such as an inflammatory T-lymphocyte, cytotoxic T-lymphocyte, regulatory T-cell or helper T-lymphocyte. According to particular embodiments, the T-cell is a cytotoxic T-lymphocyte. According to particular embodiments, the T-cell is a CD4+T-lymphocyte. According to particular embodiments, the T-cell is a CD8+T-lymphocyte. According to certain other embodiments, the immune cell is a natural killer cell.

The immune cell may be extracted from blood. Alternatively, the immune cell may be derived from a stem cell, e.g. by in vitro differentiation. The stem cell can be an adult stem cell, embryonic stem cell, cord blood stem cell, progenitor cell, bone marrow stem cell, induced pluripotent stem cell, or hematopoietic stem cell. The stem cell may a human or non-human stem cell. Representative human cells are CD34+ cells.

According to certain embodiments, the immune cell is derived from a stem cell, e.g., by in vitro differentiation. According to particular embodiments, the stem cell is a pluripotent stem cell, such as an embryonic stem cell or induced pluripotent stem cell. According to particular other embodiments, the stem cell is a multipotent stem cell, such as a haematopoietic stem cell. According to certain other embodiments, the immune cell is derived from a common lymphoid progenitor (CLP) cell, e.g., by in vitro differentiation.

According to certain embodiments, the immune cell is a mammalian immune cell. According to particular embodiments, the immune cell is a primate immune cell. According to more particular embodiments, the immune cell is a human immune cell, such as a human T-cell.

Prior to expansion and genetic modification of the immune cells of the invention, a source of cells can be obtained from a subject, such as a patient, through a variety of non-limiting methods. An immune cell, such as a T-cell, can be obtained from a number of non-limiting sources, including peripheral blood mononuclear cells, bone marrow, lymph node tissue, cord blood, thymus tissue, tissue from a site of infection, ascites, pleural effusion, spleen tissue, and tumors. According to certain embodiments, any number of immune cell lines available and known to those skilled in the art, may be used. According to other certain embodiments, the immune cell can be obtained from a healthy donor. According to other certain embodiments, the immune cell can be obtained from a patient diagnosed with malignancy. In other certain embodiments, said cell is part of a mixed population of cells which present different phenotypic characteristics.

Rare-Cutting Endonuclease

In accordance with certain embodiments of the present invention, rare-cutting endonucleases are employed which are able to selectively inactivate by DNA cleavage the gene of interest, such as the gene encoding GCN2.

The term "rare-cutting endonuclease" refers to a wild type or variant enzyme capable of catalyzing the hydrolysis (cleavage) of bonds between nucleic acids within a DNA or RNA molecule, preferably a DNA molecule. Particularly, said nuclease can be an endonuclease, more preferably a rare-cutting endonuclease which is highly specific, recognizing nucleic acid target sites ranging from 10 to 45 base pairs (bp) in length, usually ranging from 10 to 35 base pairs in length, more usually from 12 to 20 base pairs. The endonuclease according to the present invention recognizes at specific polynucleotide sequences, further referred to as "target sequence" and cleaves nucleic acid inside these target sequences or into sequences adjacent thereto, depending on the molecular structure of said endonuclease. The rare-cutting endonuclease can recognize and generate a single- or double-strand break at specific polynucleotides sequences.

In particular embodiments, a rare-cutting endonuclease according to the present invention is a RNA-guided endonuclease such as the Cas9/CRISPR complex. RNA guided endonucleases constitute a new generation of genome engineering tool where an endonuclease associates with a RNA molecule. In this system, the RNA molecule nucleotide sequence determines the target specificity and activates the endonuclease (Gasiunas, Barrangou et al. 2012; Jinek, Chylinski et al. 2012; Cong, Ran et al. 2013; Mali, Yang et al. 2013). Cas9, also named Csn1 is a large protein that participates in both crRNA biogenesis and in the destruction of invading DNA. Cas9 has been described in different bacterial species such as S. thermophiles, Listeria innocua (Gasiunas, Barrangou et al. 2012; Jinek, Chylinski et al. 2012) and S. Pyogenes (Deltcheva, Chylinski et al. 2011). The large Cas9 protein (>1200 amino acids) contains two predicted nuclease domains, namely HNH (McrA-like) nuclease domain that is located in the middle of the protein and a splitted RuvC-like nuclease domain (RNase H fold). Cas9 variant can be a Cas9 endonuclease that does not naturally exist in nature and that is obtained by protein engineering or by random mutagenesis. Cas9 variants according to the invention can for example be obtained by mutations i.e. deletions from, or insertions or substitutions of at least one residue in the amino acid sequence of a S. pyogenes Cas9 endonuclease (COG3513).

In other particular embodiments, a rare-cutting endonuclease can also be a homing endonuclease, also known under the name of meganuclease. Such homing endonucleases are well-known to the art (Stoddard, B. L., 2005). Homing endonucleases are highly specific, recognizing DNA target sites ranging from 12 to 45 base pairs (bp) in length, usually ranging from 14 to 40 bp in length. The homing endonuclease according to the invention may for example correspond to a LAGLIDADG endonuclease, to a HNH endonuclease, or to a GIY-YIG endonuclease. Preferred homing endonuclease according to the present invention can be an I-CreI variant. A "variant" endonuclease, i.e. an endonuclease that does not naturally exist in nature and that is obtained by genetic engineering or by random mutagenesis can bind DNA sequences different from that recognized by wild-type endonucleases (see international application WO2006/097854).

In other particular embodiments, a rare-cutting endonuclease can be a "Zinc Finger Nuclease" (ZFN). ZNFs are generally a fusion between the cleavage domain of the type IIS restriction enzyme, FokI, and a DNA recognition domain containing 3 or more C2H2 zinc finger motifs. The heterodimerization at a particular position in the DNA of two individual ZFNs in precise orientation and spacing leads to a double-strand break (DSB) in the DNA. The use of such chimeric endonucleases have been extensively reported in the art as reviewed by Urnov et al. (2010). Standard ZFNs fuse the cleavage domain to the C-terminus of each zinc finger domain. In order to allow the two cleavage domains to dimerize and cleave DNA, the two individual ZFNs bind opposite strands of DNA with their C-termini a certain distance apart. The most commonly used linker sequences between the zinc finger domain and the cleavage domain requires the 5' edge of each binding site to be separated by 5 to 7 bp. The most straightforward method to generate new zinc-finger arrays is to combine smaller zinc-finger "modules" of known specificity. The most common modular assembly process involves combining three separate zinc fingers that can each recognize a 3 base pair DNA sequence to generate a 3-finger array that can recognize a 9 base pair target site. Numerous selection methods have been used to generate zinc-finger arrays capable of targeting desired sequences. Initial selection efforts utilized phage display to select proteins that bound a given DNA target from a large pool of partially randomized zinc-finger arrays. More recent efforts have utilized yeast one-hybrid systems, bacterial one-hybrid and two-hybrid systems, and mammalian cells.

In other particular embodiments, a rare-cutting endonuclease is a "TALE-nuclease" (see, e.g., WO2011159369) or a "MBBBD-nuclease" (see, e.g., WO2014018601) resulting from the fusion of a DNA binding domain typically derived from Transcription Activator Like Effector proteins (TALE) or from a Modular Base-per-Base Binding domain (MBBBD), with a catalytic domain having endonuclease activity. Such catalytic domain usually comes from enzymes, such as for instance I-TevI, ColE7, NucA and Fok-I. TALE-nuclease can be formed under monomeric or dimeric forms depending of the selected catalytic domain (WO2012138927). Such engineered TALE-nucleases are commercially available under the trade name TALEN™ (Cellectis, 8 rue de la Croix Jarry, 75013 Paris, France). In general, the DNA binding domain is derived from a Transcription Activator like Effector (TALE), wherein sequence specificity is driven by a series of 33-35 amino acids repeats originating from *Xanthomonas* or *Ralstonia* bacterial proteins AvrBs3, PthXo1, AvrHah1, PthA, Tal1c as non-limiting examples. These repeats differ essentially by two amino acids positions that specify an interaction with a base pair (Boch, Scholze et al. 2009; Moscou and Bogdanove 2009). Each base pair in the DNA target is contacted by a single repeat, with the specificity resulting from the two variant amino acids of the repeat (the so-called repeat variable dipeptide, RVD). TALE binding domains may further comprise an N-terminal translocation domain responsible for the requirement of a first thymine base (T0) of the targeted sequence and a C-terminal domain that containing a nuclear localization signals (NLS). A TALE nucleic acid binding domain generally corresponds to an engineered core TALE scaffold comprising a plurality of TALE repeat sequences, each repeat comprising a RVD specific to each nucleotides base of a TALE recognition site. In the present invention, each TALE repeat sequence of said core scaffold is made of 30 to 42 amino acids, more preferably 33 or 34 wherein two critical amino acids (the so-called repeat variable dipeptide, RVD) located at positions 12 and 13 mediates the recognition of one nucleotide of said TALE binding site sequence; equivalent two critical amino acids can be located at positions other than 12 and 13 specially in TALE repeat sequence taller than 33 or 34 amino acids long. Preferably, RVDs associated with recognition of the different nucleotides are HD for recognizing C, NG for recognizing T, NI for recognizing A, NN for recognizing G or A. In another embodiment, critical amino acids 12 and 13 can be mutated towards other amino acid residues in order to modulate their specificity towards nucleotides A, T, C and G and in particular to enhance this specificity. A TALE nucleic acid binding domain usually comprises between 8 and 30 TALE repeat sequences. More preferably, said core scaffold of the present invention comprises between 8 and 20 TALE repeat sequences; again more preferably 15 TALE repeat sequences. It can also comprise an additional single truncated TALE repeat sequence made of 20 amino acids located at the C-terminus of said set of TALE repeat sequences, i.e. an additional C-terminal half-TALE repeat sequence. Other modular base-per-base specific nucleic acid binding domains (MBBBD) are described in WO 2014018601. Said MBBBD can be engineered, for instance, from newly identified proteins, namely EAV36_BURRH, E5AW43_BURRH, E5AW45_BURRH and E5AW46_BURRH proteins from the recently sequenced genome of the endosymbiont fungi *Burkholderia Rhizoxinica*. These nucleic acid binding polypeptides comprise modules of about 31 to 33 amino acids that are base specific. These modules display less than 40% sequence identity with *Xanthomonas* TALE common repeats and present more polypeptides sequence variability. The different domains from the above proteins (modules, N and C-terminals) from *Burkholderia* and *Xanthomonas* are useful to engineer new proteins or scaffolds having binding properties to specific nucleic acid sequences and may be combined to form chimeric TALE-MBBBD proteins.

As far as TALE-nucleases are concerned, suitable target sequences in the gene of interest may be identified by available software tools. For example, the software tool "Target Finder", which is provide as part of the TAL Effector Nucleotide Targeter (TALENT) 2.0 software package developed by Doyle et al. (2012), is a web-based tool (accessible thought, e.g., https://tale-nt.cac.cornell.edu/) which allows the identification of target sequences of TALE nucleases. Custom made TALE-nucleases may be ordered from Cellectis Bioresearch, 8 rue de la Croix Jarry, 75013 Paris, France.

Exemplary, non-limiting target sequences within the human GCN2 gene for inactivation by a rare-cutting endonuclease are set forth in SEQ ID NO: 3 and SEQ ID NO: 4.

According to particular embodiments, the rare-cutting endonuclease targets (e.g., binds to) a sequence set forth in SEQ ID NO: 3. According to other particular embodiments, the rare-cutting endonuclease targets (e.g., binds to) a sequence set forth in SEQ ID NO: 4.

Chimeric Antigen Receptors (CARs)

Adoptive immunotherapy, which involves the transfer of autologous antigen-specific T-cells generated ex vivo, is a promising strategy to treat cancer or viral infections. The T-cells used for adoptive immunotherapy can be generated either by expansion of antigen-specific T cells or redirection of T cells through genetic engineering (Park, Rosenberg et al. 2011). Transfer of viral antigen specific T-cells is a well-established procedure used for the treatment of transplant associated viral infections and rare viral-related malignancies. Similarly, isolation and transfer of tumor specific T cells has been shown to be successful in treating melanoma.

Novel specificities in T-cells have been successfully generated through the genetic transfer of transgenic T-cell receptors or chimeric antigen receptors (CARs) (Jena, Dotti et al. 2010). CARs are synthetic receptors consisting of a targeting moiety that is associated with one or more signaling domains in a single fusion molecule. In general, the binding moiety of a CAR consists of an antigen-binding domain of a single-chain antibody (scFv), comprising the light and variable fragments of a monoclonal antibody joined by a flexible linker. Binding moieties based on receptor or ligand domains have also been used successfully. The signaling domains for first generation CARs are derived from the cytoplasmic region of the CD3zeta or the Fc receptor gamma chains. First generation CARs have been shown to successfully redirect T cell cytotoxicity, however, they failed to provide prolonged expansion and anti-tumor activity in vivo. Signaling domains from co-stimulatory molecules including CD28, OX-40 (CD134), and 4-1BB (CD137) have been added alone (second generation) or in combination (third generation) to enhance survival and increase proliferation of CAR modified T-cells. CARs have successfully allowed T-cells to be redirected against antigens expressed at the surface of tumor cells from various malignancies including lymphomas and solid tumors (Jena, Dotti et al. 2010).

According to certain embodiments, the Chimeric Antigen Receptor expressed by the engineered immune cell is directed against an antigen selected from CD19, CD33, CD123, CS1, BCMA, CD38, 5T4, ROR1 and EGFRvIII. According to particular embodiments, the Chimeric Antigen Receptor expressed by the engineered immune cell is directed against CD33. According to other particular embodiments, the Chimeric Antigen Receptor expressed by the engineered immune cell is directed against CS1. According to other particular embodiments, the Chimeric Antigen Receptor expressed by the engineered immune cell is directed against BCMA. According to other particular embodiments, the Chimeric Antigen Receptor expressed by the engineered immune cell is directed against CD38.

According to certain embodiments, the Chimeric Antigen Receptor expressed by the engineered immune cell is directed against an antigen commonly expressed at the surface of solid tumor cells, such as 5T4, ROR1 and EGFRvIII. According to particular embodiments, the Chimeric Antigen Receptor expressed by the engineered immune cell is directed against 5T4. According to other particular embodiments, the Chimeric Antigen Receptor expressed by the engineered immune cell is directed against ROR1. According to other particular embodiments, the Chimeric Antigen Receptor expressed by the engineered immune cell is directed against EGFRvIII.

According to certain other embodiments, the Chimeric Antigen Receptor expressed by the engineered immune cell is directed against an antigen commonly expressed at the surface of liquid tumors, such as CD123. According to particular embodiments, the Chimeric Antigen Receptor expressed by the engineered immune cell is directed against CD123.

CD19 is an attractive target for immunotherapy because the vast majority of B-acute lymphoblastic leukemia (B-ALL) uniformly express CD19, whereas expression is absent on non hematopoietic cells, as well as myeloid, erythroid, and T cells, and bone marrow stem cells. Clinical trials targeting CD19 on B-cell malignancies are underway with encouraging anti-tumor responses. T-cells genetically modified to express a chimeric antigen receptor (CAR) with specificity derived from the scFv region of a CD19-specific mouse monoclonal antibody FMC63 are described in WO2013/126712.

Therefore, in accordance with particular embodiments, the Chimeric Antigen Receptor expressed by the engineered immune cell is directed against the B-lymphocyte antigen CD19.

In accordance with certain embodiments, the Chimeric Antigen Receptor is a single chain Chimeric Antigen Receptor. As an example of single-chain Chimeric Antigen Receptor to be expressed in the engineered immune cell according to the present invention is a single polypeptide that comprises at least one extracellular ligand binding domain, a transmembrane domain and at least one signal transducing domain, wherein said extracellular ligand binding domain comprises a scFV derived from the specific anti-CD19 monoclonal antibody 4G7. Once transduced into the immune cell, for instance by using retroviral or lentiviral transduction, this CAR contributes to the recognition of CD19 antigen present at the surface of malignant B-cells involved in lymphoma or leukemia.

In accordance with particular embodiments, the Chimeric Antigen Receptor is a polypeptide comprising the amino acid sequence forth in SEQ ID NO: 5 or a variant thereof comprising an amino acid sequence that has at least 70%, such as at least 80%, at least 90%, at least 95%, or at least 99%, sequence identity with the amino acid sequence set forth in SEQ ID NO: 5 over the entire length of SEQ ID NO: 5. Preferably, the variant is capable of binding CD19.

A particularly preferred Chimeric Antigen Receptor is a polypeptide comprising the amino acid sequence set forth in SEQ ID NO: 6 or a variant thereof comprising an amino acid sequence that has at least 80%, such as at least 90%, at least 95%, or at least 99%, sequence identity with the amino acid sequence set forth in SEQ ID NO: 6 over the entire length of SEQ ID NO: 6. Such variant may differ from the polypeptide set forth in SEQ ID NO: 6 in the substitution of at least one, at least two or at least three amino acid residue(s). Preferably, said variant is capable of binding CD19.

In accordance with other certain embodiments, the Chimeric Antigen Receptor may be directed against another antigen expressed at the surface of a malignant or infected cell, such as a cluster of differentiation molecule, such as CD16, CD64, CD78, CD96,CLL1, CD116, CD117, CD71, CD45, CD71, CD123 and CD138, a tumor-associated surface antigen, such as ErbB2 (HER2/neu), carcinoembryonic antigen (CEA), epithelial cell adhesion molecule (EpCAM), epidermal growth factor receptor (EGFR), EGFR variant III (EGFRvIII), CD19, CD20, CD30, CD40, disialoganglioside GD2, ductal-epithelial mucine, gp36, TAG-72, glycosphingolipids, glioma-associated antigen, β-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostase specific antigen (PSA), PAP, NY-ESO-1, LAGA-1a, p53, prostein, PSMA, surviving and telomerase, prostate-carcinoma tumor antigen-1 (PCTA-1), MAGE, ELF2M, neutrophil elastase, ephrin B2, CD22, insulin growth factor (IGF1)-I, IGF-II, IGFI receptor, mesothelin, a major histocompatibility complex (MHC) molecule presenting a tumor-specific peptide epitope, 5T4, ROR1, Nkp30, NKG2D, tumor stromal antigens, the extra domain A (EDA) and extra domain B (EDB) of fibronectin and the A1 domain of tenascin-C(TnC A1) and fibroblast associated protein (fap); a lineage-specific or tissue specific antigen such as CD3, CD4, CD8, CD24, CD25, CD33, CD34, CD133, CD138, CTLA-4, B7-1 (CD80), B7-2 (CD86), GM-CSF, cytokine receptors, endoglin, a major histocompatibility complex (MHC) molecule, BCMA (CD269, TNFRSF 17), multiple myeloma or lymphoblastic leukaemia antigen, such as one selected from TNFRSF17 (UNIPROT Q02223), SLAMF7 (UNIPROT Q9NQ25), GPRCSD (UNIPROT Q9NZD1), FKBP11 (UNIPROT Q9NYL4), KAMP3, ITGA8 (UNIPROT P53708), and FCRL5 (UNIPROT Q68SN8). a virus-specific surface antigen such as an HIV-specific antigen (such as HIV gp120); an EBV-specific antigen, a CMV-specific antigen, a HPV-specific antigen, a Lasse Virus-specific antigen, an Influenza Virus-specific antigen as well as any derivate or variant of these surface antigens.

In other certain embodiments, the Chimeric Antigen Receptor is a multi-chain Chimeric Antigen Receptor. Chimeric Antigen Receptors from the prior art introduced in T-cells have been formed of single chain polypeptides that necessitate serial appending of signaling domains. However, by moving signaling domains from their natural juxtamembrane position may interfere with their function. To overcome this drawback, the applicant recently designed a multi-chain CAR derived from FcεRI to allow normal juxtamembrane position of all relevant signaling domains. In this new architecture, the high affinity IgE binding domain of FcεRI alpha chain is replaced by an extracellular ligand-binding domain such as scFv to redirect T-cell specificity against cell targets and the N and/or C-termini tails of FcεRI beta chain are used to place costimulatory signals in normal juxtamembrane positions as described in WO 2013/176916.

Accordingly, a CAR expressed by the engineered immune cell according to the invention can be a multi-chain chimeric antigen receptor particularly adapted to the production and expansion of engineered immune cells of the present invention. Such multi-chain CARs comprise at least two of the following components:
  a) one polypeptide comprising the transmembrembrane domain of FcεRI alpha chain and an extracellular ligand-binding domain,
  b) one polypeptide comprising a part of N- and C-terminal cytoplasmic tail and the transmembrane domain of FcεRI beta chain and/or c) at least two polypeptides comprising each a part of intracytoplasmic tail and the transmembrane domain of FcεRI gamma chain, whereby different polypeptides multimerize together spontaneously to form dimeric, trimeric or tetrameric CAR.

According to such architectures, ligands binding domains and signaling domains are born on separate polypeptides. The different polypeptides are anchored into the membrane in a close proximity allowing interactions with each other. In such architectures, the signaling and co-stimulatory domains can be in juxtamembrane positions (i.e. adjacent to the cell membrane on the internal side of it), which is deemed to allow improved function of co-stimulatory domains. The multi-subunit architecture also offers more flexibility and possibilities of designing CARs with more control on T-cell activation. For instance, it is possible to include several extracellular antigen recognition domains having different specificity to obtain a multi-specific CAR architecture. It is also possible to control the relative ratio between the different subunits into the multi-chain CAR. This type of architecture is more detailed in WO2014039523.

The assembly of the different chains as part of a single multi-chain CAR is made possible, for instance, by using the different alpha, beta and gamma chains of the high affinity receptor for IgE (FcεRI) (Metzger, Alcaraz et al. 1986) to which are fused the signaling and co-stimulatory domains. The gamma chain comprises a transmembrane region and cytoplasmic tail containing one immunoreceptor tyrosine-based activation motif (ITAM) (Cambier 1995).

The multi-chain CAR can comprise several extracellular ligand-binding domains, to simultaneously bind different elements in target thereby augmenting immune cell activation and function. In one embodiment, the extracellular ligand-binding domains can be placed in tandem on the same transmembrane polypeptide, and optionally can be separated by a linker. In another embodiment, said different extracellular ligand-binding domains can be placed on different transmembrane polypeptides composing the multi-chain CAR.

The signal transducing domain or intracellular signaling domain of the multi-chain CAR(s) of the invention is responsible for intracellular signaling following the binding of extracellular ligand binding domain to the target resulting in the activation of the immune cell and immune response. In other words, the signal transducing domain is responsible for the activation of at least one of the normal effector functions of the immune cell in which the multi-chain CAR is expressed. For example, the effector function of a T cell can be a cytolytic activity or helper activity including the secretion of cytokines.

In the present application, the term "signal transducing domain" refers to the portion of a protein which transduces the effector signal function signal and directs the cell to perform a specialized function.

Preferred examples of signal transducing domain for use in single or multi-chain CAR can be the cytoplasmic sequences of the Fc receptor or T cell receptor and co-receptors that act in concert to initiate signal transduction following antigen receptor engagement, as well as any derivate or variant of these sequences and any synthetic sequence that as the same functional capability. Signal transduction domain comprises two distinct classes of cytoplasmic signaling sequence, those that initiate antigen-dependent primary activation, and those that act in an antigen-independent manner to provide a secondary or co-stimulatory signal. Primary cytoplasmic signaling sequence can comprise signaling motifs which are known as immunoreceptor tyrosine-based activation motifs of ITAMs. ITAMs are well defined signaling motifs found in the intracytoplasmic tail of a variety of receptors that serve as binding sites for syk/zap70 class tyrosine kinases. Examples of ITAM used in the invention can include as non-limiting examples those derived from TCRzeta, FcRgamma, FcRbeta, FcRepsilon, CD3gamma, CD3delta, CD3epsilon, CD5, CD22, CD79a, CD79b and CD66d. According to particular embodiments, the signaling transducing domain of the multi-chain CAR can comprise the CD3zeta signaling domain, or the intracytoplasmic domain of the FcεRI beta or gamma chains.

According to particular embodiments, the signal transduction domain of multi-chain CARs of the present invention comprises a co-stimulatory signal molecule. A co-stimulatory molecule is a cell surface molecule other than an antigen receptor or their ligands that is required for an efficient immune response.

Ligand binding-domains can be any antigen receptor previously used, and referred to, with respect to single-chain CAR referred to in the literature, in particular scFv from monoclonal antibodies.

Delivery Methods

The inventors have considered any means known in the art to allow delivery inside cells or subcellular compartments of said cells the nucleic acid molecules employed in accordance with the invention. These means include viral transduction, electroporation and also liposomal delivery means, polymeric carriers, chemical carriers, lipoplexes, polyplexes, dendrimers, nanoparticles, emulsion, natural endocytosis or phagocytose pathway as non-limiting examples.

In accordance with the present invention, the nucleic acid molecules detailed herein may be introduced in the immune cell by any suitable methods known in the art. Suitable, non-limiting methods for introducing a nucleic acid molecule into an immune cell include stable transformation methods, wherein the nucleic acid molecule is integrated into the genome of the cell, transient transformation methods wherein the nucleic acid molecule is not integrated into the genome of the cell and virus mediated methods. Said nucleic acid molecule may be introduced into a cell by, for example, a recombinant viral vector (e.g., retroviruses, adenoviruses), liposome and the like. Transient transformation methods include, for example, microinjection, electroporation or particle bombardment. In certain embodiments, the nucleic acid molecule is a vector, such as a viral vector or plasmid. Suitably, said vector is an expression vector enabling the expression of the respective polypeptide(s) or protein(s) detailed herein by the immune cell.

A nucleic acid molecule introduced into the immune cell may be DNA or RNA. In certain embodiments, a nucleic acid molecule introduced into the immune cell is DNA. In certain other embodiments, a nucleic acid molecule introduced into the immune cell is RNA, and in particular an mRNA encoding a polypeptide or protein detailed herein, which mRNA is introduced directly into the immune cell, for example by electroporation. A suitable electroporation technique is described, for example, in International Publication WO2013/176915 (in particular the section titled "Electroporation" bridging pages 29 to 30). A particular nucleic acid molecule which may be an mRNA is the nucleic acid molecule comprising a nucleotide sequence encoding a rare-cutting endonuclease able to selectively inactivate by DNA cleavage the gene encoding GCN2. Another particular nucleic acid molecule which may be an mRNA is the nucleic acid molecule comprising a nucleotide sequence encoding a rare-cutting endonuclease able to selectively inactivate by DNA cleavage the gene encoding PRDM1. A yet other particular nucleic acid molecule which may be an mRNA is the nucleic acid molecule comprising a nucleotide sequence encoding a rare-cutting endonuclease able to selectively inactivate by DNA cleavage at least one gene coding for one component of the T-cell receptor.

Nucleic acid molecules encoding the endonucleases of the present invention may be transfected under mRNA form in order to obtain transient expression and avoid chromosomal integration of foreign DNA, for example by electroporation. In this respect, the cytoPulse technology may be used which allows, by the use of pulsed electric fields, to transiently permeabilize living cells for delivery of material into the cells (U.S. Pat. No. 6,010,613 and WO 2004/083379).

Non Alloreactive Immune Cells:

T-cell receptors are cell surface receptors that participate in the activation of T-cells in response to the presentation of antigen. The TCR is generally made from two chains, alpha and beta, which assemble to form a heterodimer and associates with the CD3-transducing subunits to form the T-cell receptor complex present on the cell surface. Each alpha and beta chain of the TCR consists of an immunoglobulin-like N-terminal variable (V) and constant (C) region, a hydrophobic transmembrane domain, and a short cytoplasmic region. As for immunoglobulin molecules, the variable region of the alpha and beta chains are generated by V(D)J recombination, creating a large diversity of antigen specificities within the population of T cells. However, in contrast to immunoglobulins that recognize intact antigen, T cells are activated by processed peptide fragments in association with an MHC molecule, introducing an extra dimension to antigen recognition by T cells, known as MHC restriction. Recognition of MHC disparities between the donor and recipient through the T cell receptor leads to T cell proliferation and the potential development of GVHD. It has been shown that normal surface expression of the TCR depends on the coordinated synthesis and assembly of all seven components of the complex (Ashwell and Klusner 1990). The inactivation of TCR alpha or TCR beta can result in the elimination of the TCR from the surface of T cells preventing recognition of alloantigen and thus GVHD.

Thus, still according to the invention, engraftment of an immune cell, in particular a T-cells, may be improved by inactivating at least one gene encoding a TCR component. TCR is rendered not functional in the cells by inactivating the gene encoding TCR alpha or TCR beta.

With respect to the use of Cas9/CRISPR system, applicant has determined appropriate target sequences within the 3 exons encoding TCR, allowing a significant reduction of toxicity in living cells, while retaining cleavage efficiency. The preferred target sequences are noted in Table 1 (+ for lower ratio of TCR negative cells, ++ for intermediate ratio, +++ for higher ratio).

TABLE 1 appropriate target sequences for the guide RNA using Cas9 in T-cells

| Exon TCR | Position | Strand | Target genomic sequence | SEQ ID | efficiency |
|---|---|---|---|---|---|
| Ex1 | 78 | -1 | GAGAATCAAAATCGGTGAATAGG | 7 | +++ |
| Ex3 | 26 | 1 | TTCAAAACCTGTCAGTGATTGGG | 8 | +++ |
| Ex1 | 153 | 1 | TGTGCTAGACATGAGGTCTATGG | 9 | +++ |
| Ex3 | 74 | -1 | CGTCATGAGCAGATTAAACCCGG | 10 | +++ |
| Ex1 | 4 | -1 | TCAGGGTTCTGGATATCTGTGGG | 11 | +++ |
| Ex1 | 5 | -1 | GTCAGGGTTCTGGATATCTGTGG | 12 | +++ |
| Ex3 | 33 | -1 | TTCGGAACCCAATCACTGACAGG | 13 | +++ |
| Ex3 | 60 | -1 | TAAACCCGGCCACTTTCAGGAGG | 14 | +++ |
| Ex1 | 200 | -1 | AAAGTCAGATTTGTTGCTCCAGG | 15 | ++ |
| Ex1 | 102 | 1 | AACAAATGTGTCACAAAGTAAGG | 16 | ++ |
| Ex1 | 39 | -1 | TGGATTTAGAGTCTCTCAGCTGG | 17 | ++ |
| Ex1 | 59 | -1 | TAGGCAGACAGACTTGTCACTGG | 18 | ++ |
| Ex1 | 22 | -1 | AGCTGGTACACGGCAGGGTCAGG | 19 | ++ |
| Ex1 | 21 | -1 | GCTGGTACACGGCAGGGTCAGGG | 20 | ++ |
| Ex1 | 28 | -1 | TCTCTCAGCTGGTACACGGCAGG | 21 | ++ |
| Ex3 | 25 | 1 | TTTCAAAACCTGTCAGTGATTGG | 22 | ++ |
| Ex3 | 63 | -1 | GATTAAACCCGGCCACTTTCAGG | 23 | ++ |
| Ex2 | 17 | -1 | CTCGACCAGCTTGACATCACAGG | 24 | ++ |
| Ex1 | 32 | -1 | AGAGTCTCTCAGCTGGTACACGG | 25 | ++ |
| Ex1 | 27 | -1 | CTCTCAGCTGGTACACGGCAGGG | 26 | ++ |

TABLE 1 -continued appropriate target sequences for the guide RNA using Cas9 in T-cells

| Exon TCR | Position | Strand | Target genomic sequence | SEQ ID | efficiency |
|---|---|---|---|---|---|
| Ex2 | 12 | 1 | AAGTTCCTGTGATGTCAAGCTGG | 27 | ++ |
| Ex3 | 55 | 1 | ATCCTCCTCCTGAAAGTGGCCGG | 28 | ++ |
| Ex3 | 86 | 1 | TGCTCATGACGCTGCGGCTGTGG | 29 | ++ |
| Ex1 | 146 | 1 | ACAAAACTGTGCTAGACATGAGG | 30 | + |
| Ex1 | 86 | -1 | ATTTGTTTGAGAATCAAAATCGG | 31 | + |
| Ex2 | 3 | -1 | CATCACAGGAACTTTCTAAAAGG | 32 | + |
| Ex2 | 34 | 1 | GTCGAGAAAAGCTTTGAAACAGG | 33 | + |
| Ex3 | 51 | -1 | CCACTTTCAGGAGGAGGATTCGG | 34 | + |
| Ex3 | 18 | -1 | CTGACAGGTTTTGAAAGTTTAGG | 35 | + |
| Ex2 | 43 | 1 | AGCTTTGAAACAGGTAAGACAGG | 36 | + |
| Ex1 | 236 | -1 | TGGAATAATGCTGTTGTTGAAGG | 37 | + |
| Ex1 | 182 | 1 | AGAGCAACAGTGCTGTGGCCTGG | 38 | + |
| Ex3 | 103 | 1 | CTGTGGTCCAGCTGAGGTGAGGG | 39 | + |
| Ex3 | 97 | 1 | CTGCGGCTGTGGTCCAGCTGAGG | 40 | + |
| Ex3 | 104 | 1 | TGTGGTCCAGCTGAGGTGAGGGG | 41 | + |
| Ex1 | 267 | 1 | CTTCTTCCCCAGCCCAGGTAAGG | 42 | + |
| Ex1 | 15 | -1 | ACACGGCAGGGTCAGGGTTCTGG | 43 | + |
| Ex1 | 177 | 1 | CTTCAAGAGCAACAGTGCTGTGG | 44 | + |
| Ex1 | 256 | -1 | CTGGGGAAGAAGGTGTCTTCTGG | 45 | + |
| Ex3 | 56 | 1 | TCCTCCTCCTGAAAGTGGCCGGG | 46 | + |
| Ex3 | 80 | 1 | TTAATCTGCTCATGACGCTGCGG | 47 | + |
| Ex3 | 57 | -1 | ACCCGGCCACTTTCAGGAGGAGG | 48 | + |
| Ex1 | 268 | 1 | TTCTTCCCCAGCCCAGGTAAGGG | 49 | + |
| Ex1 | 266 | -1 | CTTACCTGGGCTGGGGAAGAAGG | 50 | + |
| Ex1 | 262 | 1 | GACACCTTCTTCCCCAGCCCAGG | 51 | + |
| Ex3 | 102 | 1 | GCTGTGGTCCAGCTGAGGTGAGG | 52 | + |
| Ex3 | 51 | 1 | CCGAATCCTCCTCCTGAAAGTGG | 53 | + |

MHC antigens are also proteins that played a major role in transplantation reactions. Rejection is mediated by T cells reacting to the histocompatibility antigens on the surface of implanted tissues, and the largest group of these antigens is the major histocompatibility antigens (MHC). These proteins are expressed on the surface of all higher vertebrates and are called HLA antigens (for human leukocyte antigens) in human cells. Like TCR, the MHC proteins serve a vital role in T cell stimulation. Antigen presenting cells (often dendritic cells) display peptides that are the degradation products of foreign proteins on the cell surface on the MHC. In the presence of a co-stimulatory signal, the T cell becomes activated, and will act on a target cell that also displays that same peptide/MHC complex. For example, a stimulated T helper cell will target a macrophage displaying an antigen in conjunction with its MHC, or a cytotoxic T cell (CTL) will act on a virally infected cell displaying foreign viral peptides.

Thus, in order to provide less alloreactive T-cells, the method of the invention can further comprise the step of inactivating or mutating at least one HLA gene.

The class I HLA gene cluster in humans comprises three major loci, B, C and A, as well as several minor loci. The class II HLA cluster also comprises three major loci, DP, DQ and DR, and both the class I and class II gene clusters are polymorphic, in that there are several different alleles of both the class I and II genes within the population. There are also several accessory proteins that play a role in HLA functioning as well. The Tap1 and Tap2 subunits are parts of the TAP transporter complex that is essential in loading peptide antigens on to the class I HLA complexes, and the LMP2 and LMP7 proteosome subunits play roles in the proteolytic degradation of antigens into peptides for display on the HLA. Reduction in LMP7 has been shown to reduce the amount of MHC class I at the cell surface, perhaps through a lack of stabilization (Fehling et al. (1999) Science 265:1234-1237). In addition to TAP and LMP, there is the tapasin gene, whose product forms a bridge between the TAP complex and the HLA class I chains and enhances peptide loading. Reduction in tapasin results in cells with impaired MHC class I assembly, reduced cell surface expression of the MHC class I and impaired immune responses (Grandea et al. (2000) Immunity 13:213-222 and Garbi et al. (2000) Nat. Immunol. 1:234-238). Any of the above genes may be inactivated as part of the present invention as disclosed, for instance in WO 2012/012667.

Activation and Expansion of Immune Cells

The method according to the invention may include a further step of activating and/or expanding the immune cell(s). This can be done prior to or after genetic modification of the immune cell(s), using the methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005. According to these methods, the immune cells of the invention can be expanded by contact with a surface having attached thereto an agent that stimulates a CD3 TCR complex associated signal and a ligand that stimulates a co-stimulatory molecule on the surface of the immune cells.

In particular, T-cell populations may be stimulated in vitro such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T-cells cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4+ T cells or CD8+ T cells, an anti-CD3 antibody and an anti-CD28 antibody. For example, the agents providing each signal may be in solution or coupled to a surface. As those of ordinary skill in the art can readily appreciate, the ratio of particles to cells may depend on particle size relative to the target cell. In further embodiments of the present invention, the cells, such as T cells, are combined with agent-coated beads, the beads and the cells are subsequently separated, and then the cells are cultured. In an alternative embodiment, prior to culture, the agent-coated beads and cells are not separated but are cultured together. Cell surface proteins may be ligated by allowing paramagnetic beads to which anti-CD3 and anti-CD28 are attached (3×28 beads) to contact the T cells. In one embodiment the cells (for example, 4 to 10 T cells) and beads (for example, DYNABEADS® M-450 CD3/CD28 T paramagnetic beads at a ratio of 1:1) are combined in a buffer, preferably PBS (without divalent cations such as, calcium and magnesium). Again, those of ordinary skill in the art can readily appreciate any cell concentration may be used. The mixture may be cultured for several hours (about 3 hours) to about 14 days or any hourly integer value in between. In another embodiment, the mixture may be cultured for 21 days. Conditions appropriate for T cell culture include an appropriate media (e.g., Minimal Essential Media or RPMI Media 1640 or, X-vivo 5, (Lonza)) that may contain factors necessary for proliferation and viability, including serum (e.g., fetal bovine or human serum), interleukin-2 (IL-2), insulin, IFN-g, 1L-4, 1L-7, GM-CSF, -10, -2, 1L-15, TGFp, and TNF- or any other additives for the growth of cells known to the skilled artisan. Other additives for the growth of cells include, but are not limited to, surfactant, plasmanate, and reducing agents such as N-acetyl-cysteine and 2-mercaptoethanoi. Media can include RPMI 1640, A1M-V, DMEM, MEM, a-MEM, F-12, X-Vivo 1, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% CO2). T cells that have been exposed to varied stimulation times may exhibit different characteristics In another particular embodiment, said immune cell(s) can be expanded by co-culturing with tissue or cells. Said cells can also be expanded in vivo, for example in the subject's blood after administrating said cell into the subject.

Engineered Immune Cells

As a result of the present invention, engineered immune cells can be obtained having improved characteristics. In particular, the present invention provides an engineered, preferably isolated, immune cell which is characterized in that a gene encoding GCN2 and/or a gene encoding PRDM1 is inactivated or repressed.

According to certain embodiments, an engineered immune cell is provided wherein a gene encoding GCN2 (e.g., the human GCN2 gene) is inactivated.

According to certain other embodiments, an engineered immune cell is provided wherein a gene encoding GCN2 (e.g., the human GCN2 gene) is repressed.

According to certain other embodiments, an engineered immune cell is provided wherein a gene encoding PRDM1 (e.g., the human PRDM1 gene) is inactivated.

According to certain other embodiments, an engineered immune cell is provided wherein a gene encoding PRDM1 (e.g., the human PRDM1 gene) is repressed.

According to certain other embodiments, an engineered immune cell is provided wherein both a gene encoding GCN2 (e.g., the human GCN2 gene) and a gene encoding PRDM1 (e.g., the human PRDM1 gene) are inactivated.

According to certain other embodiments, an engineered immune cell is provided wherein both a gene encoding GCN2 (e.g., the human GCN2 gene) and a gene encoding PRDM1 (e.g., the human PRDM1 gene) are repressed.

According to certain other embodiments, an engineered immune cell is provided wherein a gene encoding GCN2 (e.g., the human GCN2 gene) is inactivated and a gene encoding PRDM1 (e.g., the human PRDM1 gene) is repressed.

According to certain other embodiments, an engineered immune cell is provided wherein a gene encoding GCN2 (e.g., the human GCN2 gene) is repressed and a gene encoding PRDM1 (e.g., the human PRDM1 gene) is inactivated.

According to certain embodiments, an engineered immune cell is obtained which expresses a rare-cutting endonuclease able to selectively inactivate by DNA cleavage, preferably double-strand break, a gene encoding GCN2. According to particular embodiments, said immune cell comprises an exogenous nucleic acid molecule comprising a nucleotide sequence encoding said rare-cutting endonuclease. According to more particular embodiments, said rare-cutting endonuclease is a TALE-nuclease, meganuclease, zinc-finger nuclease (ZFN), or RNA guided endonuclease. Hence, in accordance with a specific embodiment, the rare-cutting endonuclease is a TALE-nuclease. In accordance with another specific embodiment, the rare-cutting endonuclease is a meganuclease. In accordance with another specific embodiment, the rare-cutting endonuclease is a zinc-finger nuclease. In accordance with yet another specific embodiment, the rare-cutting endonuclease is a RNA guided endonuclease, such as Cas9.

According to certain embodiments, an engineered immune cell is obtained which expresses a rare-cutting endonuclease able to selectively inactivate by DNA cleavage, preferably double-strand break, a gene encoding PRDM1. According to particular embodiments, said immune cell comprises an exogenous nucleic acid molecule comprising a nucleotide sequence encoding said rare-cutting endonuclease. According to more particular embodiments, said rare-cutting endonuclease is a TALE-nuclease, meganuclease, zinc-finger nuclease (ZFN), or RNA guided endonuclease. Hence, in accordance with a specific embodiment, the rare-cutting endonuclease is a TALE-nuclease. In accordance with another specific embodiment, the rare-cutting endonuclease is a meganuclease. In accordance with another specific embodiment, the rare-cutting endonuclease is a zinc-finger nuclease. In accordance with yet another specific embodiment, the rare-cutting endonuclease is a RNA guided endonuclease, such as Cas9.

According to certain other embodiments, an engineered immune cell is obtained which expresses a rare-cutting endonuclease able to selectively inactivate by DNA cleavage, preferably double-strand break, a gene encoding GCN2 and a rare-cutting endonuclease able to selectively inactivate by DNA cleavage, preferably double-strand break, a gene encoding PRDM1. According to particular embodiments, said immune cell comprises one or more exogenous nucleic acid molecules comprising one or more nucleotide sequences encoding said rare-cutting endonucleases.

According to certain embodiments, the engineered immune cell further expresses a rare-cutting endonuclease able to selectively inactivate by DNA cleavage, preferably double-strand break, at least one gene coding for a component of the T-cell receptor, such as TCR alpha. According to particular embodiments, said immune cell comprises an exogenous nucleic acid molecule comprising a nucleotide sequence encoding said rare-cutting endonuclease.

According to certain embodiments, the engineered immune cell further expresses a Chimeric Antigen Receptor (CAR) directed against at least one antigen expressed at the surface of a malignant cell. According to particular embodiments, said immune cell comprises an exogenous nucleic acid molecule comprising a nucleotide sequence encoding said CAR.

It is understood that the details given herein in particularly with respect to the rare-cutting endonuclease able to selectively inactivate by DNA cleavage the gene encoding GCN2, the rare-cutting endonuclease able to selectively inactivate by DNA cleavage the gene encoding PRDM1, the rare-cutting endonuclease able to selectively inactivate by DNA cleavage at least one gene coding for a component of the T-cell receptor (TCR), and the Chimeric Antigen Receptor also apply to this aspect of the invention.

Further, in the scope of the present invention is also encompassed a cell line obtained from an engineered immune cell according to the invention.

As a result of the present invention, engineered immune cells can be used as therapeutic products, ideally as an "off the shelf" product, for use in the treatment or prevention of medical conditions such as cancer.

Therapeutic Applications

Immune cells obtainable in accordance with the present invention are intended to be used as a medicament, and in particular for treating cancer in a patient (e.g. a human patient) in need thereof. Accordingly, the present invention provides engineered immune cells for use as a medicament. Particularly, the present invention provides engineered immune cells for use in the treatment of a cancer. Also provided are compositions, particularly pharmaceutical compositions, which comprise at least one engineered immune cell of the present invention. In certain embodiments, a composition may comprise a population of engineered immune cells of the present invention.

The treatment can be ameliorating, curative or prophylactic. It may be either part of an autologous immunotherapy or part of an allogenic immunotherapy treatment. By autologous, it is meant that cells, cell line or population of cells used for treating patients are originating from said patient or from a Human Leucocyte Antigen (HLA) compatible donor. By allogeneic is meant that the cells or population of cells used for treating patients are not originating from said patient but from a donor.

The invention is particularly suited for allogenic immunotherapy, insofar as it enables the transformation of immune cells, such as T-cells, typically obtained from donors, into non-alloreactive cells. This may be done under standard protocols and reproduced as many times as needed. The resultant modified immune cells may be pooled and administrated to one or several patients, being made available as an "off the shelf" therapeutic product.

The treatments are primarily to treat patients diagnosed with cancer. Particular cancers to be treated according to the invention are those which have solid tumors, but may also concern liquid tumors. Adult tumors/cancers and pediatric tumors/cancers are also included.

According to certain embodiments, the engineered immune cell(s) or composition is for use in the treatment of a cancer, and more particularly for use in the treatment of a solid or liquid tumor. According to particular embodiments, the engineered immune cell(s) or composition is for use in the treatment of a solid tumor. According to other particular embodiments, the engineered immune cell(s) or composition is for use in the treatment of a liquid tumor.

According to particular embodiments, the engineered immune cell(s) or composition is for use in the treatment of a cancer selected from the group consisting of lung cancer, small lung cancer, breast cancer, uterine cancer, prostate cancer, kidney cancer, colon cancer, liver cancer, pancreatic cancer, and skin cancer. According to more particular embodiments, the engineered immune cell(s) or composition is for use in the treatment of lung cancer. According to other more particular embodiments, the engineered immune cell(s) or composition is for use in the treatment of small lung cancer. According to other more particular embodiments, the engineered immune cell(s) or composition is for use in the treatment of breast cancer. According to other more particular embodiments, the engineered immune cell(s) or composition is for use in the treatment of uterine cancer. According to other more particular embodiments, the engineered immune cell(s) or composition is for use in the treatment of prostate cancer. According to other more particular embodiments, the engineered immune cell(s) or composition is for use in the treatment of kidney cancer.

According to other more particular embodiments, the engineered immune cell(s) or composition is for use in the treatment of colon cancer. According to other more particular embodiments, the engineered immune cell(s) or composition is for use in the treatment of liver cancer. According to other more particular embodiments, the engineered immune cell(s) or composition is for use in the treatment of pancreatic cancer. According to other more particular embodiments, the engineered immune cell(s) or composition is for use in the treatment of skin cancer.

According to other particular embodiments, the engineered immune cell(s) or composition is for use in the treatment of a sarcoma.

According to other particular embodiments, the engineered immune cell(s) or composition is for use in the treatment of a carcinoma. According to more particular embodiments, the engineered immune cell or composition is for use in the treatment of renal, lung or colon carcinoma.

According to other particular embodiments, the engineered immune cell(s) or composition is for use in the treatment of leukemia, such as acute lymphoblastic leukemia (ALL), acute myeloid leukemia (AML), chronic lymphocytic leukemia (CLL), chronic myelogenous leukemia (CML), and chronic myelomonocytic leukemia (CMML). According to more particular embodiments, the engineered immune cell(s) or composition is for use in the treatment of acute lymphoblastic leukemia (ALL). According to other more particular embodiments, the engineered immune cell(s) or composition is for use in the treatment of acute myeloid leukemia (AML). According to other more particular embodiments, the engineered immune cell(s) or composition is for use in the treatment of chronic lymphocytic leukemia (CLL). According to other more particular embodiments, the engineered immune cell(s) or composition is for use in the treatment of chronic myelogenous leukemia (CML). According to other more particular embodiments, the engineered immune cell(s) or composition is for use in the treatment of chronic myelomonocytic leukemia (CMML).

According to other particular embodiments, the engineered immune cell(s) or composition is for use in the treatment of lymphoma, such as B-cell lymphoma. According to more particular embodiments, the engineered immune cell(s) or composition is for use in the treatment of primary CNS lymphoma. According to other more particular embodiments, the engineered immune cell(s) or composition is for use in the treatment of Hodgkin's lymphoma. According to other more particular embodiments, the engineered immune cell(s) or composition is for use in the treatment of Non-Hodgkin's lymphoma. According to more particular embodiments, the engineered immune cell(s) or composition is for use in the treatment of diffuse large B cell lymphoma (DLBCL). According to other more particular embodiments, the engineered immune cell(s) or composition is for use in the treatment of Follicular lymphoma. According to other more particular embodiments, the engineered immune cell(s) or composition is for use in the treatment of marginal zone lymphoma (MZL). According to other more particular embodiments, the engineered immune cell(s) or composition is for use in the treatment of Mucosa-Associated Lymphatic Tissue lymphoma (MALT). According to other more particular embodiments, the engineered immune cell(s) or composition is for use in the treatment of small cell lymphocytic lymphoma. According to other more particular embodiments, the engineered immune cell(s) or composition is for use in the treatment of mantle cell lymphoma (MCL). According to other more particular embodiments, the engineered immune cell(s) or composition is for use in the treatment of Burkitt lymphoma. According to other more particular embodiments, the engineered immune cell(s) or composition is for use in the treatment of primary mediastinal (thymic) large B-cell lymphoma. According to other more particular embodiments, the engineered immune cell(s) or composition is for use in the treatment of Waldenström macroglobulinemia. According to other more particular embodiments, the engineered immune cell(s) or composition is for use in the treatment of nodal marginal zone B cell lymphoma (NMZL). According to other more particular embodiments, the engineered immune cell(s) or composition is for use in the treatment of splenic marginal zone lymphoma (SMZL). According to other more particular embodiments, the engineered immune cell(s) or composition is for use in the treatment of intravascular large B-cell lymphoma. According to other more particular embodiments, the engineered immune cell(s) or composition is for use in the treatment of Primary effusion lymphoma. According to other more particular embodiments, the engineered immune cell(s) or composition is for use in the treatment of lymphomatoid granulomatosis. According to other more particular embodiments, the engineered immune cell(s) or composition is for use in the treatment of T cell/histiocyte-rich large B-cell lymphoma. According to other more particular embodiments, the engineered immune cell(s) or composition is for use in the treatment of primary diffuse large B-cell lymphoma of the CNS (Central Nervous System). According to other more particular embodiments, the engineered immune cell(s) or composition is for use in the treatment of primary cutaneous diffuse large B-cell lymphoma. According to other more particular embodiments, the engineered immune cell(s) or composition is for use in the treatment of EBV positive diffuse large B-cell lymphoma of the elderly. According to other more particular embodiments, the engineered immune cell(s) or composition is for use in the treatment of diffuse large B-cell lymphoma associated with inflammation. According to other more particular embodiments, the engineered immune cell(s) or composition is for use in the treatment of ALK-positive large B-cell lymphoma. According to other more particular embodiments, the engineered immune cell(s) or composition is for use in the treatment of plasmablastic lymphoma. According to other more particular embodiments, the engineered immune cell(s) or composition is for use in the treatment of Large B-cell lymphoma arising in HHV8-associated multicentric Castleman disease.

According to certain embodiment, the engineered immune cell originates from a patient, e.g. a human patient, to be treated. According to certain other embodiment, the engineered immune cell originates from at least one donor.

The treatment can take place in combination with one or more therapies selected from the group of antibodies therapy, chemotherapy, cytokines therapy, dendritic cell therapy, gene therapy, hormone therapy, laser light therapy and radiation therapy.

According to certain embodiments, immune cells of the invention can undergo robust in vivo immune cell expansion upon administration to a patient, and can persist in the body fluids for an extended amount of time, preferably for a week, more preferably for 2 weeks, even more preferably for at least one month. Although the immune cells according to the invention are expected to persist during these periods, their life span into the patient's body are intended not to exceed a year, preferably 6 months, more preferably 2 months, and even more preferably one month.

The administration of the cells or population of cells according to the present invention may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous or intralymphatic injection, or intraperitoneally. In one embodiment, the cell compositions of the present invention are preferably administered by intravenous injection.

The administration of the cells or population of cells can consist of the administration of 104-109 cells per kg body weight, preferably 105 to 106 cells/kg body weight including all integer values of cell numbers within those ranges. The cells or population of cells can be administered in one or more doses. In another embodiment, said effective amount of cells are administered as a single dose. In another embodiment, said effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions within the skill of the art. An effective amount means an amount which provides a therapeutic or prophylactic benefit.

The dosage administrated will be dependent upon the age, health and weight of the recipient, kind of concurrent treatment, if any, frequency of treatment and the nature of the effect desired.

In other embodiments, said effective amount of cells or composition comprising those cells are administered parenterally. Said administration can be an intravenous administration. Said administration can be directly done by injection within a tumor.

In certain embodiments, cells are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or nataliziimab treatment for MS patients or efaliztimab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAMPATH, anti-CD3 antibodies or other antibody therapies, cytoxin, fludaribine, cyclosporin, FK506, rapamycin, mycoplienolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 1 1; Henderson et al., Immun. 73:316-321, 1991; Bierer et al., Citrr. Opin. mm n. 5:763-773, 93). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH, In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded genetically engineered immune cells of the present invention. In an additional embodiment, expanded cells are administered before or following surgery.

Also encompassed within this aspect of the invention are methods for treating a patient in need thereof, comprising a) providing at least one engineered immune cell of the present invention, preferably a population of said immune cell; and b) administering said immune cell or population to said patient.

Also encompassed within this aspect of the invention are methods for preparing a medicament using at least one engineered immune cell of the present invention, and preferably a population of said immune cell. Accordingly, the present invention provides the use of at least one engineered immune cell of the present invention, and preferably a population of said immune cell, in the manufacture of a medicament. Preferably, such medicament is for use in the treatment of a disease as specified above.

Other Definitions

Amino acid residues in a polypeptide sequence are designated herein according to the one-letter code, in which, for example, Q means Gln or Glutamine residue, R means Arg or Arginine residue and D means Asp or Aspartic acid residue.

Amino acid substitution means the replacement of one amino acid residue with another, for instance the replacement of an Arginine residue with a Glutamine residue in a peptide sequence is an amino acid substitution.

Nucleotides are designated as follows: one-letter code is used for designating the base of a nucleoside: a is adenine, t is thymine, c is cytosine, and g is guanine. For the degenerated nucleotides, r represents g or a (purine nucleotides), k represents g or t, s represents g or c, w represents a or t, m represents a or c, y represents t or c (pyrimidine nucleotides), d represents g, a or t, v represents g, a or c, b represents g, t or c, h represents a, t or c, and n represents g, a, t or c.

"As used herein, "nucleic acid" or "polynucleotides" refers to nucleotides and/or polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Nucleic acids can be either single stranded or double stranded.

by "DNA target", "DNA target sequence", "target DNA sequence", "nucleic acid target sequence", "target sequence", or "processing site" is intended a polynucleotide sequence that can be targeted and processed by a rare-cutting endonuclease according to the present invention. These terms refer to a specific DNA location, preferably a genomic location in a cell, but also a portion of genetic material that can exist independently to the main body of genetic material such as plasmids, episomes, virus, transposons or in organelles such as mitochondria as non-limiting example. As non-limiting examples of RNA guided target sequences, are those genome sequences that can hybridize the guide RNA which directs the RNA guided endonuclease to a desired locus.

By "delivery vector" or "delivery vectors" is intended any delivery vector which can be used in the present invention to put into cell contact (i.e "contacting") or deliver inside cells or subcellular compartments (i.e "introducing") agents/chemicals and molecules (proteins or nucleic acids) needed in the present invention. It includes, but is not limited to liposomal delivery vectors, viral delivery vectors, drug delivery vectors, chemical carriers, polymeric carriers, lipoplexes, polyplexes, dendrimers, microbubbles (ultrasound contrast agents), nanoparticles, emulsions or other appropriate transfer vectors. These delivery vectors allow delivery of molecules, chemicals, macromolecules (genes, proteins), or other vectors such as plasmids, or penetrating peptides. In these later cases, delivery vectors are molecule carriers.

The terms "vector" or "vectors" refer to a nucleic acid molecule capable of transporting another nucleic acid to which it has been linked. A "vector" in the present invention includes, but is not limited to, a viral vector, a plasmid, a RNA vector or a linear or circular DNA or RNA molecule which may consists of a chromosomal, non-chromosomal, semi-synthetic or synthetic nucleic acids. Preferred vectors are those capable of autonomous replication (episomal vector) and/or expression of nucleic acids to which they are linked (expression vectors). Large numbers of suitable vectors are known to those of skill in the art and commercially available.

Viral vectors include retrovirus, adenovirus, parvovirus (e. g. adenoassociated viruses), coronavirus, negative strand RNA viruses such as orthomyxovirus (e. g., influenza virus), rhabdovirus (e. g., rabies and vesicular stomatitis virus), paramyxovirus (e. g. measles and Sendai), positive strand RNA viruses such as picornavirus and alphavirus, and double-stranded DNA viruses including adenovirus, herpesvirus (e. g., Herpes Simplex virus types 1 and 2, Epstein-Barr virus, cytomegalovirus), and poxvirus (e. g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D type viruses, HTLV-BLV group, lentivirus, spumavirus (Coffin, J. M., Retroviridae: The viruses and their replication, In Fundamental Virology, Third Edition, B. N. Fields, et al., Eds., Lippincott-Raven Publishers, Philadelphia, 1996).

By "lentiviral vector" is meant HIV-Based lentiviral vectors that are very promising for gene delivery because of their relatively large packaging capacity, reduced immunogenicity and their ability to stably transduce with high efficiency a large range of different cell types. Lentiviral vectors are usually generated following transient transfection of three (packaging, envelope and transfer) or more plasmids into producer cells. Like HIV, lentiviral vectors enter the target cell through the interaction of viral surface glycoproteins with receptors on the cell surface. On entry, the viral RNA undergoes reverse transcription, which is mediated by the viral reverse transcriptase complex. The product of reverse transcription is a double-stranded linear viral DNA, which is the substrate for viral integration in the DNA of infected cells. By "integrative lentiviral vectors (or LV)", is meant such vectors as non limiting example, that are able to integrate the genome of a target cell. At the opposite by "non integrative lentiviral vectors (or NILV)" is meant efficient gene delivery vectors that do not integrate the genome of a target cell through the action of the virus integrase.

Delivery vectors and vectors can be associated or combined with any cellular permeabilization techniques such as sonoporation or electroporation or derivatives of these techniques.

By "cell" or "cells" is intended any eukaryotic living cells, primary cells and cell lines derived from these organisms for in vitro cultures.

By "primary cell" or "primary cells" are intended cells taken directly from living tissue (i.e. biopsy material) and established for growth in vitro, that have undergone very few population doublings and are therefore more representative of the main functional components and characteristics of tissues from which they are derived from, in comparison to continuous tumorigenic or artificially immortalized cell lines.

As non-limiting examples cell lines can be selected from the group consisting of CHO-K1 cells; HEK293 cells; Caco2 cells; U2-OS cells; NIH 3T3 cells; NSO cells; SP2 cells; CHO-S cells; DG44 cells; K-562 cells, U-937 cells; MRC5 cells; IMR90 cells; Jurkat cells; HepG2 cells; HeLa cells; HT-1080 cells; HCT-116 cells; Hu-h7 cells; Huvec cells; Molt 4 cells.

All these cell lines can be modified by the method of the present invention to provide cell line models to produce, express, quantify, detect, study a gene or a protein of interest; these models can also be used to screen biologically active molecules of interest in research and production and various fields such as chemical, biofuels, therapeutics and agronomy as non-limiting examples.

By "stem cell" is meant a cell that has the capacity to self-renew and the ability to generate differentiated cells. More explicitly, a stem cell is a cell which can generate daughter cells identical to their mother cell (self-renewal) and can produce progeny with more restricted potential (differentiated cells).

By "NK cells" is meant natural killer cells. NK cells are defined as large granular lymphocytes and constitute the third kind of cells differentiated from the common lymphoid progenitor generating B and T lymphocytes.

by "mutation" is intended the substitution, deletion, insertion of up to one, two, three, four, five, six, seven, eight, nine, ten, eleven, twelve, thirteen, fourteen, fifteen, twenty, twenty five, thirty, fourty, fifty, or more nucleotides/amino acids in a polynucleotide (cDNA, gene) or a polypeptide sequence. The mutation can affect the coding sequence of a gene or its regulatory sequence. It may also affect the structure of the genomic sequence or the structure/stability of the encoded mRNA.

by "variant(s)", it is intended a repeat variant, a variant, a DNA binding variant, a TALE-nuclease variant, a polypeptide variant obtained by mutation or replacement of at least one residue in the amino acid sequence of the parent molecule.

by "functional variant" is intended a catalytically active mutant of a protein or a protein domain; such mutant may have the same activity compared to its parent protein or protein domain or additional properties, or higher or lower activity.

By "gene" is meant the basic unit of heredity, consisting of a segment of DNA arranged in a linear manner along a chromosome, which codes for a specific protein or segment of protein. A gene typically includes a promoter, a 5' untranslated region, one or more coding sequences (exons), optionally introns, a 3' untranslated region. The gene may further comprise a terminator, enhancers and/or silencers.

As used herein, the term "locus" is the specific physical location of a DNA sequence (e.g. of a gene) on a chromosome. The term "locus" can refer to the specific physical location of a rare-cutting endonuclease target sequence on a chromosome. Such a locus can comprise a target sequence that is recognized and/or cleaved by a rare-cutting endonuclease according to the invention. It is understood that the locus of interest of the present invention can not only qualify a nucleic acid sequence that exists in the main body of genetic material (i.e. in a chromosome) of a cell but also a portion of genetic material that can exist independently to said main body of genetic material such as plasmids, episomes, virus, transposons or in organelles such as mitochondria as non-limiting examples.

The term "cleavage" refers to the breakage of the covalent backbone of a polynucleotide. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. Double stranded DNA, RNA, or DNA/RNA hybrid cleavage can result in the production of either blunt ends or staggered ends.

By "fusion protein" is intended the result of a well-known process in the art consisting in the joining of two or more genes which originally encode for separate proteins or part of them, the translation of said "fusion gene" resulting in a single polypeptide with functional properties derived from each of the original proteins.

"identity" refers to sequence identity between two nucleic acid molecules or polypeptides. Identity can be determined by comparing a position in each sequence which may be aligned for purposes of comparison. When a position in the compared sequence is occupied by the same base or amino acid, then the molecules are identical at that position. A degree of similarity or identity between nucleic acid or amino acid sequences is a function of the number of identical or matching nucleotides or amino acids at positions shared by the nucleic acid or amino acid sequences, respectively. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting. For example, polypeptides having at least 70%, 85%, 90%, 95%, 98% or 99% identity to specific polypeptides described herein and preferably exhibiting substantially the same functions, as well as polynucleotide encoding such polypeptides, are contemplated.

"co-stimulatory ligand" refers to a molecule on an antigen presenting cell that specifically binds a cognate co-stimulatory molecule on a T-cell, thereby providing a signal which, in addition to the primary signal provided by, for instance, binding of a TCR/CD3 complex with an MHC molecule loaded with peptide, mediates a T cell response, including, but not limited to, proliferation activation, differentiation and the like. A co-stimulatory ligand can include but is not limited to CD7, B7-1 (CD80), B7-2 (CD86), PD-L1, PD-L2, 4-1BBL, OX40L, inducible costimulatory igand (ICOS-L), intercellular adhesion molecule (ICAM, CD30L, CD40, CD70, CD83, HLA-G, MICA, M1CB, HVEM, lymphotoxin beta receptor, 3/TR6, ILT3, ILT4, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as but not limited to, CD27, CD28, 4-IBB, OX40, CD30, CD40, PD-1, ICOS, lymphocyte function-associated antigen-1 (LFA-1), CD2, CD7, LTGHT, NKG2C, B7-H3, a ligand that specifically binds with CD83.

A "co-stimulatory molecule" refers to the cognate binding partner on a Tcell that specifically binds with a co-stimulatory ligand, thereby mediating a co-stimulatory response by the cell, such as, but not limited to proliferation. Co-stimulatory molecules include, but are not limited to an MHC class I molecule, BTLA and Toll ligand receptor.

A "co-stimulatory signal" as used herein refers to a signal, which in combination with primary signal, such as TCR/CD3 ligation, leads to T cell proliferation and/or upregulation or downregulation of key molecules.

The term "extracellular ligand-binding domain" as used herein is defined as an oligo- or polypeptide that is capable of binding a ligand. Preferably, the domain will be capable of interacting with a cell surface molecule. For example, the extracellular ligand-binding domain may be chosen to recognize a ligand that acts as a cell surface marker on target cells associated with a particular disease state. Thus examples of cell surface markers that may act as ligands include those associated with viral, bacterial and parasitic infections, auto-immune disease and cancer cells.

The term "subject" or "patient" as used herein includes all members of the animal kingdom including non-human primates and humans.

The above written description of the invention provides a manner and process of making and using it such that any person skilled in this art is enabled to make and use the same, this enablement being provided in particular for the subject matter of the appended claims, which make up a part of the original description.

Where a numerical limit or range is stated herein, the endpoints are included. Also, all values and sub ranges within a numerical limit or range are specifically included as if explicitly written out.

Having generally described this invention, a further understanding can be obtained by reference to certain specific examples, which are provided herein for purposes of illustration only, and are not intended to be limiting unless otherwise specified.

EXAMPLES

Example 1: T-Cell Sensitivity to Arginase Activity

To verify that T-cells were sensitive to arginine deprivation by arginase I activity in their microenvironment, Xcico15 media complemented with 5% human AB serum and 20 ng/ml human IL2 (100 µl per well in a 96-well plate) was incubated with increasing concentrations of recombinant arginase I (0.5 to 1500 ng/µl).

After 3 days at 4° C., human T-cells that had previously been transfected (PulseAgile) with mRNA encoding a TRAC specific TALE nuclease or no RNA were resuspended in the arginase-treated media. After 72 hourss at 37° C., cell viability was measured by flow cytometry. The results are depicted in FIG. 2.

Figure 2:
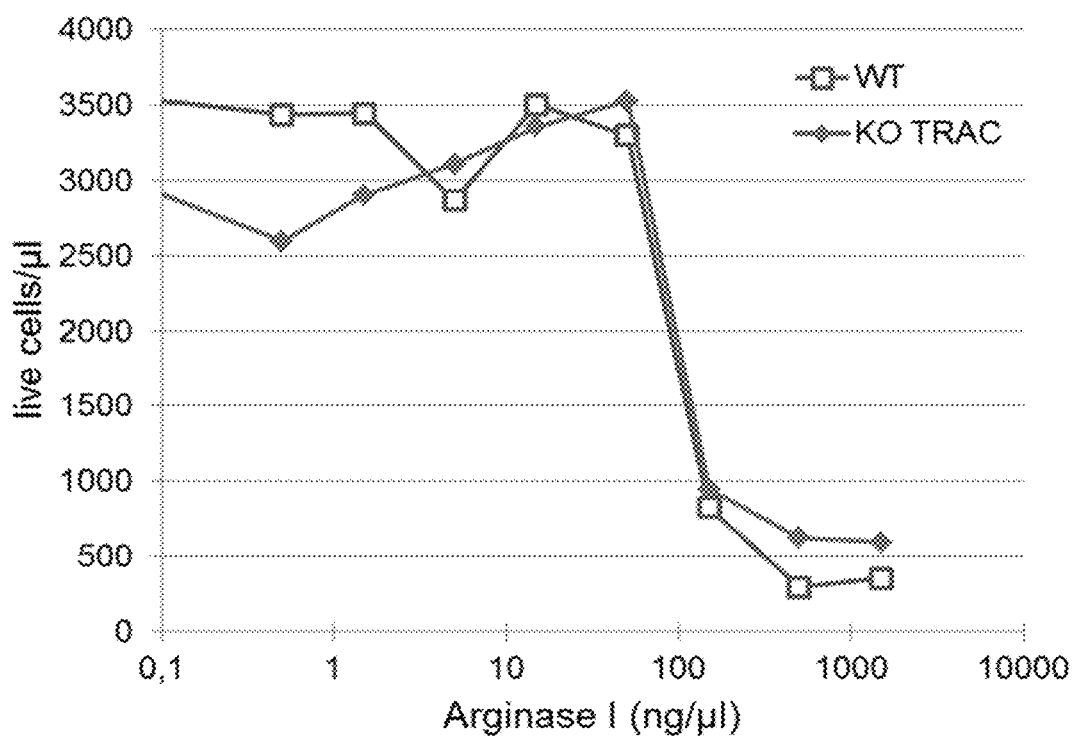
FIG. 2: Measurement by flow cytometry of live cell concentration of human T-cells transfected with mRNA encoding a TALE nuclease specific for TRAC (KO TRAC) or untransfected human T-cells (WT; wild type) after exposure for 72 hours at 37° C. to increasing concentrations of recombination arginase I (0.5-1500 ng/ml) in Xvivo15 medium complemented with 5% human AB serum and 20 ng/ml human IL2 (100 µl per well in a 96-well plate). The data confirm that both untransfected T-cells and T-cells treated with TRAC specific TALE nuclease are sensitive to arginine deprivation in vitro.

As can be seen from FIG. 2, increasing concentrations of arginase, and thus decreasing concentrations of arginine in the media leads to a drastic decrease in viable T-cells. These results suggest that both T-cells treated with TRAC specific TALE nuclease (KO TRAC) and untreated T-cells (WT) are sensitive to arginine deprivation in their microenvironment in vitro.

Example 2: GCN2 Disruption by Use of TALE Nucleases

Two TALE nucleases (GCN2_1 and GCN2_2) were designed to disrupt the GCN2 gene in human T-cells. mRNA encoding TALE nucleases targeting the human GCN2 gene were ordered from Cellectis Bioresearch (8, rue de la Croix Jarry, 75013 Paris). Table 2 below indicates the target sequence cleaved by the respective TALE nuclease.

TABLE 2

TALE nucleases targeting human GCN2 gene

| | target sequence |
|---|---|
| GCN2_1 | TGGATTTGAGGGTTAAATGCCCACCTACCTATCCAGATG TGTGAGTACA (SEQ ID NO: 3) |
| GCN2_2 | TTGTAGGAAATGGTAAACATCGGGCAAACTCCTCAGGAA GGTCTAGGTA (SEQ ID NO: 4) |

Human T-cells were transfected with mRNA encoding either of said TALE nucleases. Control cells were transfected without RNA. 3 days post transfection genomic DNA was isolated and subjected to T7 endonuclease assay to detect TALE nuclease activity. The results are depicted in FIG. 3.

Figure 3:
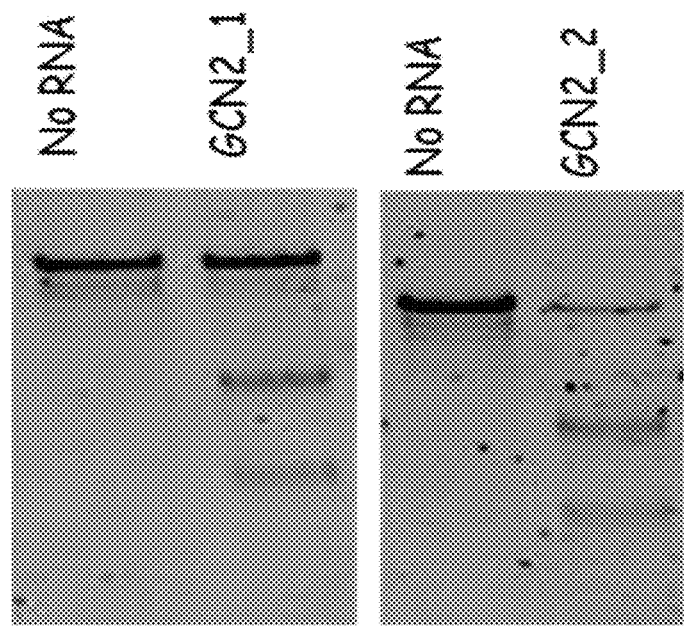
FIG. 3: Results of T7 endonuclease assay on genomic DNA isolated from human T-cells transfected with mRNA encoding GCN2 specific TALE nucleases. The presence of lower molecular bands compared to samples obtained from untransfected T-cells indicates cleavage activity of both TALENs used.

As can be seen from FIG. 3, the presence of lower molecular bands compared to the sample without RNA transfection clearly indicated cleavage activity of both TALE nucleases.

To test whether GCN2 disruption conferred resistance to arginine deprivation by arginase, TALEN treated T cells as well as control cells were incubated in RPM11640 medium prepared without arginine where arginine was added in increasing concentration. After 72h incubation at 37° C., cell viability was measured by flow cytometry.

Figure 4:
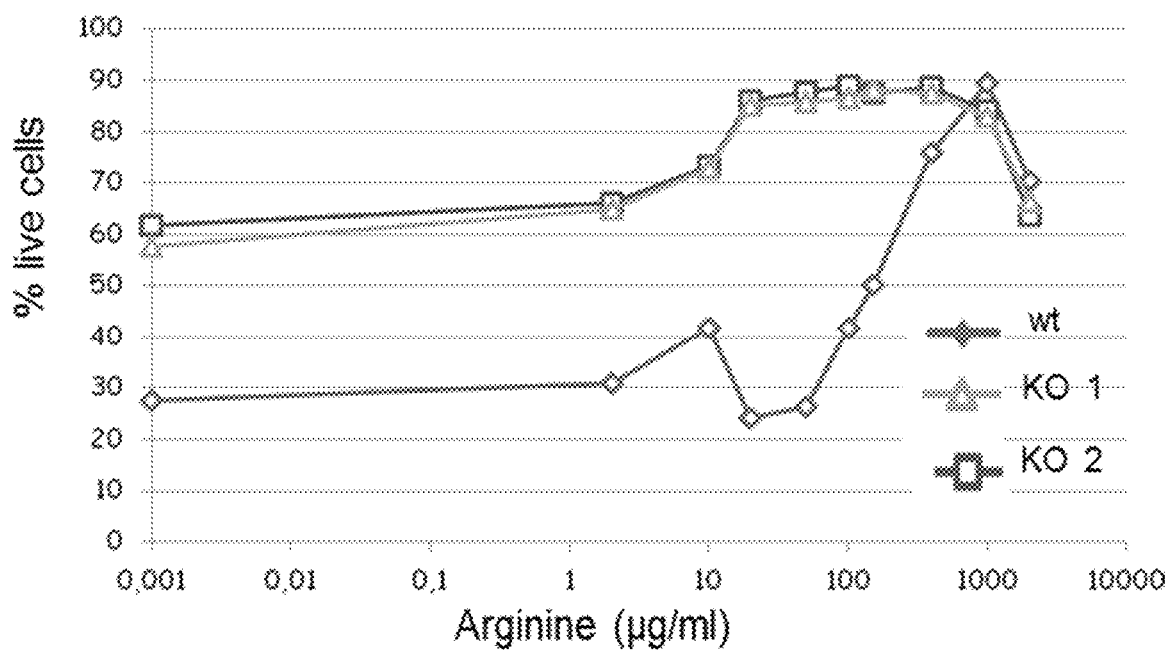
FIG. 4: Measurement by flow cytometry of live cells concentration of human T-cells transfected with mRNA encoding GCN2 specific TALE nucleases (KO1 and KO2) or untransfected human T-cells (WT, wild type) after incubation for 72 hours at 37° C. in RPM11640 medium with increasing concentrations of arginine added. The data show cells treated with GCN2 specific TALE nuclease survive better at lower concentrations of arginine, and thus provides resistance to immunosuppression in a tumor microenvironment where arginase is secreted.

As can be seen from FIG. 4, T-cells treated with GCN2 TALEN survived better at lower concentrations of arginine. This suggests that immune cells, and especially T-cells, having a disrupted GCN2 gene, and thus do not express the GCN2 protein in a functional form, provide resistance to immunosuppression in a tumor microenvironment where arginase is secreted.

LIST OF REFERENCES CITED IN THE DESCRIPTION

Ashwell, J. D. and R. D. Klusner (1990). "Genetic and mutational analysis of the T-cell antigen receptor." *Annu Rev Immunol* 8: 139-67.

Betts, M. R., J. M. Brenchley, et al. (2003). "Sensitive and viable identification of antigen-specific CD8+ T cells by a flow cytometric assay for degranulation." *J Immunol Methods* 281(1-2): 65-78.

Bierer B. E. et al. (1993) "Cyclosporin A and FK506: molecular mechanisms of immunosuppression and probes for transplantation biology." *Curr Opin Immunol* 5(5): 763-73.

Boch, J., H. Scholze, et al. (2009). "Breaking the code of DNA binding specificity of TAL-type III effectors." *Science* 326(5959): 1509-12.

Cambier, J. C. (1995). "Antigen and Fc receptor signaling. The awesome power of the immunoreceptor tyrosine-based activation motif (ITAM)." *J Immunol* 155(7): 3281-5.

Cong, L., F. A. Ran, et al. (2013). "Multiplex genome engineering using CRISPR/Cas systems." *Science* 339 (6121): 819-23.

Critchlow, S. E. and S. P. Jackson (1998). "DNA end-joining: from yeast to man." *Trends Biochem Sci* 23(10): 394-8.

Deltcheva, E., K. Chylinski, et al. (2011). "CRISPR RNA maturation by trans-encoded small RNA and host factor RNase III." *Nature* 471(7340): 602-7.

Doyle E. L., Booher, N. J., et al. (2012). "TAL Effector-Nucleotide Targeter (TALE-NT) 2.0: tools for TAL effector design and target prediction." *Nucleic Acids Res* 40(W1): W117-22

Gasiunas, G. et al. (2012). "Cas9-crRNA ribonucleoprotein complex mediates specific DNA cleavage for adaptive immunity in bacteria." *Proc Natl Acad Sci USA* 109(39): E2579-86.

Henderson D. J. et al. (1991). "Comparison of the effects of FK-506, cyclosporin A and rapamycin on IL-2 production." *Immunology* 73(3): 316-21.

Jena, B., G. Dotti, et al. (2010). "Redirecting T-cell specificity by introducing a tumor-specific chimeric antigen receptor." *Blood* 116(7): 1035-44.

Jinek, M., K. Chylinski, et al. (2012). "A programmable dual-RNA-guided DNA endonuclease in adaptive bacterial immunity." *Science* 337(6096): 816-21.

Lindstrom V., Aittoniemi J., Jylhava J., Eklund C., Hurme M., Paavonen T., Oja S. S., Itala-Remes M., Sinisalo M. (2012). "Indoleamine 2 3-dioxygenase activity and expression in patients with chronic lymphocytic leukemia". *Clin Lymphoma Myeloma Leuk.* 5:363-513.

Liu L. et al. (1991). "Calcineurin is a common target of cyclophilin-cyclosporin A and FKBP-FK506 complexes." *Cell* 66(4): 807-15.

Ma, J. L., E. M. Kim, et al. (2003). "Yeast Mre11 and Rad1 proteins define a Ku-independent mechanism to repair double-strand breaks lacking overlapping end sequences." *Mol Cell Biol* 23(23): 8820-8.

Mali, P., L. Yang, et al. (2013). "RNA-guided human genome engineering via Cas9." *Science* 339(6121): 823-6.

Metzger, H., G. Alcaraz, et al. (1986). "The receptor with high affinity for immunoglobulin E." *Annu Rev Immunol* 4: 419-70

Moscou, M. J. and A. J. Bogdanove (2009). "A simple cipher governs DNA recognition by TAL effectors." *Science* 326(5959): 1501.

Munn, D. H., et al. (2004). "Expression of Indoleamine 2,3-dioxygenase by plasmacytoid dendritic cells in tumor-draining lymph nodes". *J. Clin. Invest.* 114:280-290.

Mussai F., et al. (2013). "Acute myeloid leukemia creates an arginase-dependent immunosuppressive microenvironment". *Blood.* 122(5):749-758.

Park, T. S., S. A. Rosenberg, et al. (2011). "Treating cancer with genetically engineered T cells." *Trends Biotechnol* 29(11): 550-7.

Rutella, S. et al. (2013). "Indoleamine 2,3-dioxygenase-1 (IDO1) expression by childhood acute myeloid leukemia restrains IFNgamma production by T cells and may portend an unfavourable prognosis (P2157)". *Journal for ImmunoTherapy of Cancer* 1(Suppl 1): P172.

Stoddard, B. L. (2005). "Homing endonuclease structure and function." *Q Rev Biophys* 38(1): 49-95.

Suer G S, Yoruk Y, Cakir E, Yorulmaz F, Gulen S. (1999) "Arginase and ornithine, as markers in human non-small cell lung carcinoma". *Cancer Biochem Biophys.* 17:125-31.

Swarts, D. C. et al. (2014) "The evolutionary journey of Argonaute proteins". *Nature Struct. Mol. Biol.* 21, 743-753

Urnov F. D. et al. (2010) "Genome editing with engineered zinc finger nucleases" *Nature reviews Genetics* 11:636-646

The invention claimed is:

1. An isolated population of engineered immune cells comprising inactivation of PR domain zinc finger protein 1 (PRDM1) and general control nonderepressible 2 (GCN2) genes, wherein said inactivation is by cleavage with a rare-cutting endonuclease.

2. The population of engineered immune cells according to claim 1, wherein said inactivation is by cleavage with a rare-cutting endonuclease.

3. The population of engineered immune cells according to claim 1, wherein said GCN2 is human GCN2 set forth in SEQ ID NO: 1 or a functional variant thereof which has at least about 80% sequence identity with the human GCN2 set forth in SEQ ID NO: 1 over the entire length of SEQ ID NO: 1.

4. The population of engineered immune cells according to claim 1, wherein said PRDM1 is human PRDM1 set forth in SEQ ID NO: 2 or a functional variant thereof which has at least about 80% sequence identity with the human PRDM1 set forth in SEQ ID NO: 2 over the entire length of SEQ ID NO: 2.

5. The population of engineered immune cells according to claim 1, wherein said immune cells express a rare-cutting endonuclease able to selectively inactivate by DNA cleavage a gene encoding GCN2.

6. The population of engineered immune cells according to claim 5, wherein said rare-cutting endonuclease binds to a sequence set forth in SEQ ID NO: 3 or SEQ ID NO: 4.

7. The population of engineered immune cells according to claim 1, wherein said immune cells express a rare-cutting endonuclease able to selectively inactivate by DNA cleavage the gene encoding said PRDM1.

8. The population of engineered immune cells according to claim 2, wherein said immune cells comprise an exogenous nucleic acid molecule comprising a nucleotide sequence encoding said rare-cutting endonuclease.

9. The population of engineered immune cells according to claim 8, wherein said nucleic acid molecule is a vector allowing said rare-cutting endonuclease to be expressed by said immune cells.

10. The population of engineered immune cells according to claim 9, wherein said nucleic acid molecule is a transfected mRNA.

11. The population of engineered immune cells according to claim 2, wherein said rare-cutting endonuclease is a TALE-nuclease, meganuclease, zinc-finger nuclease (ZFN), or RNA or DNA guided endonuclease.

12. The population of engineered immune cells according to claim 11, wherein said rare-cutting endonuclease is a TALE-nuclease.

13. The population of engineered immune cells according to claim 11, wherein said rare-cutting endonuclease is a RNA-guided endonuclease.

14. The population of engineered immune cells according to claim 13, wherein said RNA-guided endonuclease is Cas9.

15. The population of engineered immune cells according to claim 1, further characterized in that at least one gene encoding a component of the TCR receptor of said cells is inactivated.

16. The population of engineered immune cells according to claim 1, wherein said immune cells express a Chimeric Antigen Receptor (CAR) directed against at least one antigen expressed at the surface of a malignant cell.

17. The population of engineered immune cells according to claim 16, wherein said immune cells comprise an exogenous nucleic acid molecule comprising a nucleotide sequence encoding said CAR.

18. The population of engineered immune cells according to claim 17, wherein said CAR is directed against an antigen selected from CD19, CD33, CD123, CS1, BCMA, CD38, 5T4, ROR1 and EGFRVIII.

19. The population of engineered immune cells according to claim 1, wherein said immune cell is, or is derived from, a T-cell.

* * * * *